United States Patent [19]
Takami et al.

[11] Patent Number: 5,833,836
[45] Date of Patent: Nov. 10, 1998

[54] METHOD AND DEVICE FOR MEASURING OXYGEN CONCENTRATION

[75] Inventors: Masayuki Takami, Kariya; Satoshi Haseda, Okazaki; Tomomichi Mizoguchi, Nagoya, all of Japan

[73] Assignee: Denso Corporation, Kariya, Japan

[21] Appl. No.: 764,652

[22] Filed: Dec. 11, 1996

[30] Foreign Application Priority Data

Dec. 18, 1995 [JP] Japan ................................. 7-328913
Jul. 5, 1996 [JP] Japan ................................. 8-176402

[51] Int. Cl.⁶ .............................................. G01N 27/407
[52] U.S. Cl. ....................... 205/785; 204/424; 204/425; 204/426; 204/428
[58] Field of Search .................... 204/408, 421–429; 205/783.5, 784, 784.5, 785

[56] References Cited

U.S. PATENT DOCUMENTS

| | | |
|---|---|---|
| 4,472,262 | 9/1984 | Kondo et al. . |
| 4,543,176 | 9/1985 | Harada et al. . |
| 4,586,476 | 5/1986 | Asayama et al. ............. 204/426 |
| 4,626,338 | 12/1986 | Konde et al. . |
| 5,391,284 | 2/1995 | Hotzel et al. ............ 204/426 |
| 5,405,521 | 4/1995 | Nakamori et al. . |

FOREIGN PATENT DOCUMENTS 0145073 6/1985 European Pat. Off. .
2290618 6/1995 United Kingdom .

OTHER PUBLICATIONS

U.S. application No. 08/605,782, Feb. 22, 1996, Mizoguchi et al.

*Primary Examiner*—T. Tung
*Attorney, Agent, or Firm*—Nixon & Vanderhye P.C.

[57] ABSTRACT

To achieve change-over from detection of an internal resistance of an oxygen sensor S to detection of a threshold current effectively in a short time, a positive desired voltage for measuring a threshold current is applied to an oxygen sensor S to detect the threshold current and then a negative voltage for measuring a temperature is applied to the oxygen sensor S for a short time to detect an internal resistance of the oxygen sensor. After that, when the voltage applied to the oxygen sensor S is restored to a positive desired voltage for measuring the threshold current, by applying a voltage higher than this positive desired voltage temporarily to the oxygen sensor S, discharge or recharge of electric charges due to electrostatic capacitance components of the oxygen sensor S is completed quickly to reduce the time required for convergence to the threshold current when the voltage is changed. As a result, it is possible to reduce the time during which the threshold current cannot be detected.

15 Claims, 15 Drawing Sheets

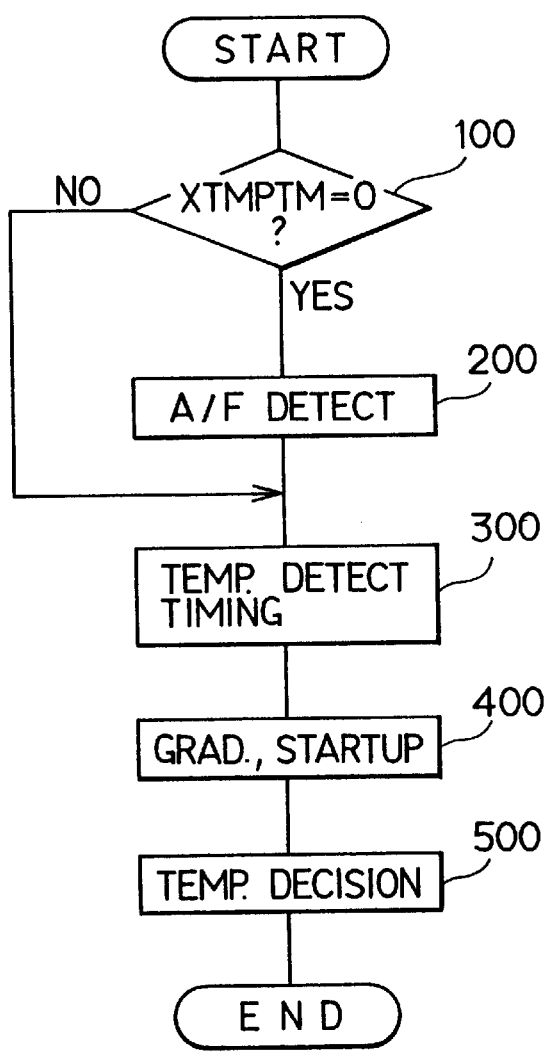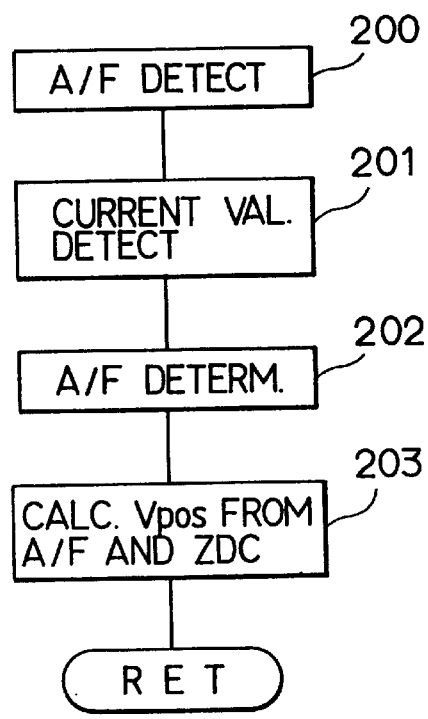

METHOD AND DEVICE FOR MEASURING OXYGEN CONCENTRATION

CROSS-REFERENCE TO RELATED APPLICATIONS

The present application is related to and claims priority from Japanese Patent Application Nos. Hei 7-328913 and 8-176402, incorporated herein by reference.

BACKGROUND OF THE INVENTION

1. Field of the Invention

The present invention relates to an oxygen concentration measuring device for measuring an air-fuel ratio or oxygen concentration of exhaust gas discharged from an internal combustion engine.

2. Description of Related Art

Conventionally, in this type of oxygen concentration measuring device, as disclosed in U.S. Pat. No. 5,405,521, for example, based on the fact that internal resistance of the threshold current type oxygen sensor varies depending on the temperature of the element and that a current-voltage characteristic curve for determining the internal resistance of the oxygen sensor passes through the origin as shown by a locus 1 in FIGS. 1A and 1C, the oxygen sensor is positively biased during a first period by a positive voltage (threshold current measuring voltage) in the vicinity of the center of the threshold current domain, while it is negatively biased during a second period by a negative voltage (temperature measuring voltage). Current flowing through the oxygen sensor is detected during the first and second periods. The oxygen concentration is determined on the basis of the current detected during the first period while the internal resistance of the oxygen sensor is determined on the basis of the current and the voltage detected during the second period, to detect the temperature of the element.

When the bias voltage is changed from the positive side to the negative side or vice versa with respect to the oxygen sensor, the electromotive force which was induced in the oxygen sensor when a threshold current was flowing therethrough is discharged. As shown by the locus 1 in FIG. 1B, the detected current converges to its stable state after reaching its positive and negative peaks. Accordingly, the temperature cannot be determined until the detected current converges from its negative peak to its stable state and the threshold current cannot be detected until the detected current converges from its positive peak to its stable state. Since the oxygen concentration cannot be detected during those periods, it is impossible to ensure a period sufficient to detect the oxygen concentration. Therefore, in the above-described conventional devices, a period for determining the temperature is reduced by detecting a converging current which is still on the way from its negative peak to its stable state and thereby estimating a convergence value thereof.

Although the above description refers to a case in which the temperature measuring, voltage is lower than the threshold current measuring voltage, it is also possible to provide a construction in which the temperature measuring voltage is higher than the threshold current measuring voltage.

However, in a conventional construction described above, no appropriate measure has been taken to reduce the time during which the oxygen concentration cannot be detected when the voltage to be supplied to the oxygen sensor is changed from the temperature measuring voltage to the threshold current measuring voltage.

SUMMARY OF THE INVENTION

In view of the above problems of the prior art, an object of the present invention is to provide an oxygen concentration sensing device capable of effectively reducing the time during which the oxygen concentration cannot be detected when the voltage to be supplied to the oxygen sensor is changed from the temperature measuring voltage to the threshold current measuring voltage.

Therefore, according to the present invention, when the voltage to be supplied to the oxygen sensor is changed from a temperature measuring voltage lower/higher than the threshold current measuring voltage to the threshold current measuring voltage, the threshold current measuring voltage is restored after a voltage higher/lower than the threshold current measuring voltage is supplied for a short period. As a result, the time required for the detected current to be stabilized from its peak to the threshold current can be reduced. Furthermore, it is also possible to reduce effectively the period during which the oxygen concentration cannot be detected when the voltage to be supplied to the oxygen sensor is changed from the temperature measuring voltage to the threshold current measuring voltage.

Furthermore, when the threshold current of the oxygen sensor is being detected, the voltage supplied to the oxygen sensor is reduced until the electromotive force generated in the oxygen sensor decreases to a predetermined value. When the electromotive force has reached that value, the temperature measuring voltage is supplied to the oxygen sensor for a short time so that the time required for the detected current to be stabilized from its negative peak can be reduced. Consequently, the period during which the oxygen concentration cannot be detected can be reduced further.

As an alternative to the threshold current type, an oxygen sensor of an integrated type which is designed to detect the oxygen concentration from a pumping current may also be used.

Other objects and features of the invention will appear in the course of the description thereof, which follows.

BRIEF DESCRIPTION OF THE DRAWINGS

Additional objects and advantages of the present invention will be more readily apparent from the following detailed description of preferred embodiments thereof when taken together with the accompanying drawings in which:

FIGS. 5–9 are flowcharts showing the operation of the microprocessor of the first embodiment;

DETAILED DESCRIPTION OF THE PRESENTLY PREFERRED EXEMPLARY EMBODIMENTS

Figure 2:
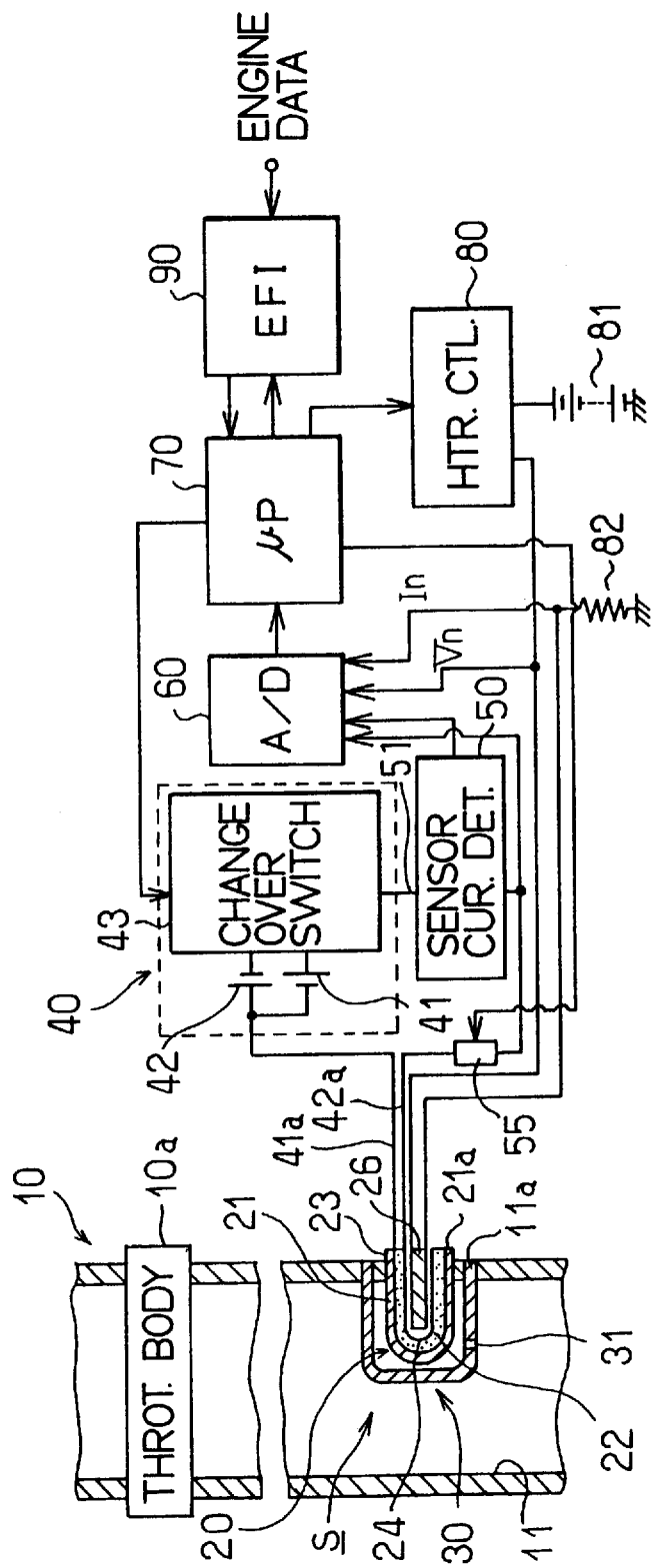
FIG. 2 is a block diagram showing a first preferred embodiment of the present invention.

Hereinbelow, a first embodiment of the present invention will be described with reference to the accompanying drawings. FIG. 2 shows an example of an oxygen concentration measuring device employed in an internal combustion engine 10 disposed in a vehicle. The oxygen concentration measuring device is provided with a threshold current type oxygen sensor S. The oxygen sensor S is mounted in an exhaust pipe 11 extending from a main body 10a of the internal combustion engine 10. The oxygen sensor S includes a sensor main body 20 and a cover 30 having a U-shaped cross-section. The bottom portion of the sensor main body 20 is inserted into a mounting hole portion 11a formed through part of a wall of the exhaust pipe 11 and extends towards the interior of the exhaust pipe 11.

The sensor main body 20 includes a diffusion resistant layer 21 having a cup-shaped cross-section. An opening end portion 21a of the diffusion resisting layer 21 is inserted into the mounting hole portion 11a of the exhaust pipe 11. The diffusion resisting layer 21 is formed by plasma melting ejection method or the like, using $ZrO_2$ or the like. Furthermore, the sensor main body 20 includes a solid electrolyte layer 22. The solid electrolyte layer 22, which is made of an oxygen ion conductive oxide sintered body and has a cup-shaped cross-section, is deposited uniformly on an inner surface of the diffusion resisting layer 21 through an exhaust gas side electrode layer 23 having a cup-shaped cross-section. An atmosphere side electrode layer 24 which also has a cup-shaped cross-section is secured uniformly to an inner surface of the solid electrolyte layer 22. In this case, in order to obtain sufficient porosity, both the exhaust gas side electrode layer 23 and the atmosphere side electrode layer 24 are formed of a noble metal of high catalytic activity, such as platinum, by chemical plating or the like. The area and the thickness of the exhaust gas side electrode layer 23 are about 10 to 100 $mm^2$ and 0.5 to 2.0 $\mu m$, respectively. On the other hand, those of the atmosphere side electrode layer 24 are greater than 10 $mm^2$ and about 0.5 to 2.0 $\mu m$, respectively.

The sensor main body 20 thus constructed generates a concentration electromotive force at the theoretical air fuel ratio and produces a threshold current corresponding to an oxygen concentration in the lean domain with respect to the theoretical air fuel ratio point. In this case, the threshold current corresponding to the oxygen concentration is determined by the area of the exhaust gas side electrode layer 23 and the thickness, the porosity and the average pore diameter of the diffusion resisting layer 21. The sensor main body 20 is able to detect the oxygen concentration by using linear characteristics thereof. However, since a temperature higher than about 650° C. is required to activate the sensor main body 20 and a temperature range in which the sensor main body 20 is activated is narrow, the active range thereof cannot be controlled only by heating with exhaust gas from the internal combustion engine. For this reason, heating control using a heater 26 is carried out, which will be described later. In the rich side domain with respect to the theoretical air-fuel ratio, the concentration of carbon monoxide (CO), which is unburnt gas, varies substantially linearly with respect to the air-fuel ratio and a threshold current corresponding thereto is produced.

Figure 3A:
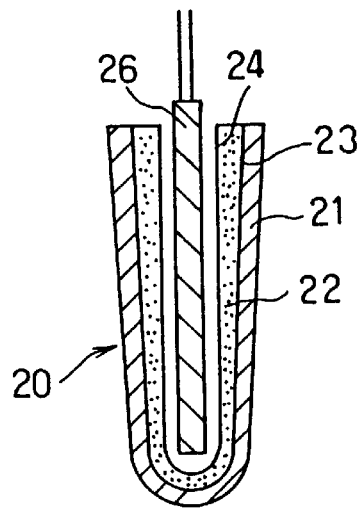
FIG. 3A is an enlarged cross section of the oxygen sensor main body according to the first embodiment and FIG. 3B is a characteristic diagram showing the voltage-current characteristics of the oxygen sensor as a parameter of temperature thereof.

Now referring to FIGS. 3A and 3B, the voltage-current characteristics of the sensor main body 20 using the temperature thereof as a parameter will be explained. These voltage-current characteristics indicate that there is a linear relationship between the current flowing into the solid electrolyte layer 22 of the sensor main body 20 which is proportional to the oxygen concentration (air-fuel ratio) detected by the oxygen sensor S and the voltage applied to the solid electrolyte layer 22. When the sensor main body 20 is in an active state at a temperature T=T1, its stable state is represented by a characteristic graph L1 as indicated by solid lines in FIG. 3B. In this case, threshold currents of the sensor main body are represented by straight line portions of the characteristic graph L1 parallel to the voltage axis V. Increase or decrease in the threshold current corresponds to increase or decrease in the air-fuel ratio (i.e., lean or rich). When the temperature T of the sensor main body 20 is at T2, which is lower than T1, the voltage-current characteristics are represented by a characteristic graph L2 as indicated by broken lines in FIG. 3B. In this case, threshold currents of the sensor main body 20 at T=T2 are represented by straight line portions of the characteristic graph L2 parallel to the voltage axis V. These threshold currents are almost in accordance with the threshold currents indicated by the characteristic graph L1.

Figure 3B:
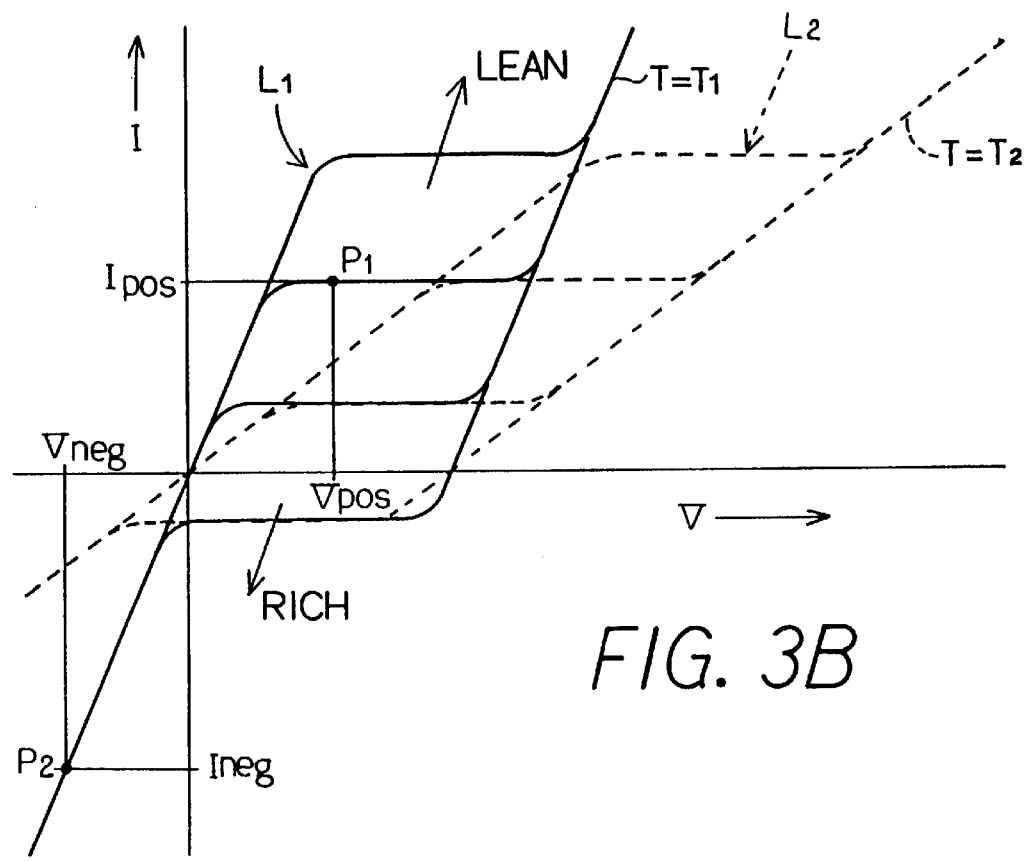

In the characteristic graph L1, when a positive voltage Vpos is applied to the solid electrolyte layer 22 in the sensor main body 20, current flowing through the sensor main body 20 is the threshold current Ipos at that time (refer to point P1 in FIG. 3B). Here, it is desirable to set the voltage Vpos of a positive desired value to a value corresponding to a position in the vicinity of the center portion of the straight line portion of FIG. 3B, throughout which the threshold current Ipos flows. That is, because the position in the vicinity of the center portion of the straight line as shown in FIG. 3B throughout which the threshold current Ipos flows varies depending on the threshold current Ipos (concentration of oxygen) and the temperature (temperature of the element) of the sensor main body 20, the voltage Vpos of the positive desired value is preferably set to be positioned in the vicinity of the center portion of the straight line portion as shown in FIG. 3B throughout which the threshold current Ipos flows, in accordance with the threshold current Ipos (concentration of oxygen) and the temperature (temperature of the element) of the sensor main body 20.

On the contrary, when a negative voltage Vneg is applied to the solid electrolyte layer 22 in the sensor main body 20, current flowing through the sensor main body 20 is a negative temperature current Ineg determined by a point P2, which is independent of the oxygen concentration and proportional only to the temperature.

The sensor main body 20 includes a heater 26 accommodated in an atmosphere side electrode layer 24. The heater 26 heats the atmosphere side electrode layer 24, the solid electrolyte layer 22, the exhaust gas side electrode layer 23 and the diffusion resisting layer 21 with exothermic energy thereof. In this case, the heater 26 has a heat capacity sufficient to activate the sensor main body 20. The sensor main body 20 is covered by a cover 30 and the opening portion thereof is inserted into a portion of a peripheral wall of the exhaust pipe 11. A small hole 31 is formed through a portion of a peripheral wall of the cover 30 for communicating the exterior of the cover 30 with the interior thereof. In this way, the cover 30 keeps the temperature of the sensor main body 20 constant by preventing the sensor main body 20 from being exposed to exhaust gas.

Furthermore, as shown in FIG. 2, the oxygen concentration measuring device is provided with a bias control circuit 40. The bias control circuit 40 comprises a positive biasing DC power source 41, a negative biasing DC power source 42 and a switching circuit 43. A negative electrode of the DC power source 41 is connected to one end of the exhaust gas side electrode layer 23 through a wire 41a, while a positive electrode of the DC power source 42 is connected to the other end of the exhaust gas side electrode layer 23 through the wire 41a. The switching circuit 43 is designed to connect only the positive electrode of the DC power source 41 to an input terminal 51 of a current detecting circuit 50 in a first switching state thereof and only the negative electrode of the DC power source 42 to the input terminal 51 of the current detecting circuit 50 in a second switching state thereof. The switching circuit 43 is connected to the atmosphere side electrode layer 24 via the input terminal 51, the current detecting circuit 50, a semiconductor switch 55 and another wire 42a.

Consequently, when the semiconductor switch 55 is in a conductive state and the switching circuit 43 is in a first switching state, the DC power source 41 biases the solid electrolyte layer 22 positively and thereby allows current to flow through the solid electrolyte layer 22 in a positive direction. On the other hand, when the semiconductor switch 55 is in the conductive state and the switching circuit 43 is in a second switching state, the DC power source 42 biases the solid electrolyte layer 22 negatively and thereby allows current to flow through the solid electrolyte layer 22 in a negative direction. In this case, terminal voltages of the DC power sources 41 and 42 correspond to the applied voltages Vpos and Vneg respectively. According to the construction of the switching circuit 43, the switching state thereof can be controlled in accordance with a bias command Vr from a microprocessor 70 and the voltage applied at the time of positive biasing can be varied in accordance with the bias command Vr from the microprocessor 70.

The current detecting circuit 50 detects current flowing from the atmosphere side electrode layer 24 in the sensor main body 20 to the switching circuit 43 or vice versa, i.e., current flowing through the solid electrolyte layer 22, using a current detecting resistor (not shown) and outputs it to an A-D converter 60. The A-D converter 60 converts the current thus detected by the current detecting circuit 50, the voltage Vn applied to the heater 26 and the current In flowing through the heater 26 into digital values, which are outputted to the microprocessor 70. The microprocessor 70 includes a CPU, ROM, RAM and the like (not shown) and cooperates with the A-D converter 60 to execute a program.

In executing this program, a calculating operation required to control a bias control circuit 40, a heating control circuit 80 and a fuel injection control device (hereinafter referred to as an EFI unit) 90 is performed. The program described above is previously stored in a ROM of the microprocessor 70.

The semiconductor switch 55 is usually kept in the conductive state in response to a signal from the microprocessor 70 to supply positive and negative bias voltages from the DC power sources 41, 42 to the sensor main body 20. Because an electromotive force generated in the sensor main body 20 is detected when the threshold current Ipos is flowing through the oxygen sensor S, the microprocessor 55 is periodically brought into an instantaneously interrupted state by an instantaneously interrupting signal from the microprocessor 70, so that the supply of bias voltages from the DC power source 41 for positive biasing to the sensor main body 20 is periodically interrupted instantaneously.

The heating control circuit 80 executes heating control of the heater 26 based on the control by the microprocessor 70 by implementing the ON/OFF control and the duty control of power to be supplied to the heater 26 from a battery 81 which serves as a power supply, depending on the temperatures of the oxygen sensor S and the heater 26. Furthermore, the current In flowing through the heater 26 is detected by the current detecting resistor 82 and supplied to the A-D converter 60. In addition, the EFI unit 90 executes fuel injection control according to what is known about the internal, combustion engine such as amount of exhaust gas (air-fuel ratio), number of rotations, flow rate of intake air, negative pressure in air intake pipe, temperature of cooling water, or the like of the internal combustion engine 10, based on the control by the microprocessor 70.

Figure 4:
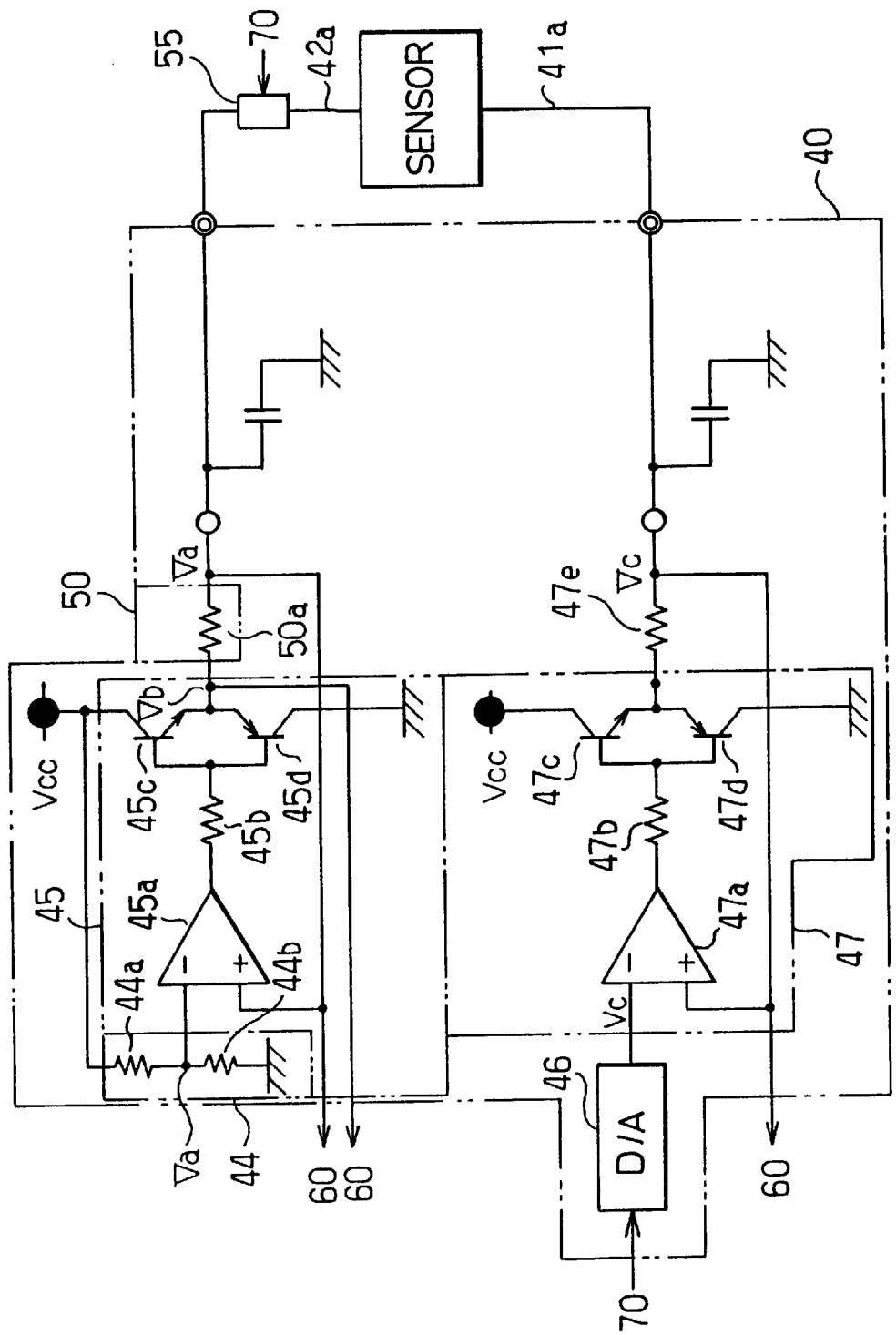
FIG. 4 is a schematic diagram of a bias control circuit according to the first embodiment.

FIG. 4 shows a concrete configuration of an electric circuit of the bias control circuit 40. A reference voltage circuit 44 divides a constant voltage Vcc by means of voltage dividing resistors 44a, 44b to obtain a constant reference voltage Va. A first voltage supplying circuit 45 supplies a voltage equal to the reference voltage Va of the reference voltage circuit 44 to one terminal (the wire 42a to be connected to the atmosphere side electrode layer 24) of the oxygen sensor S. The circuit 45 includes an operational amplifier 45a in which a negative input terminal thereof is connected to a voltage dividing point of the voltage dividing resistors 44a, 44b and a positive input terminal thereof is connected to one terminal of the oxygen sensor S through the semiconductor switch 55, a resistor 45b one end of which is connected to the output terminal of the operational amplifier 45a, and NPN and PNP transistors 45c and 45d whose bases are connected to the other end of the resistor 45b respectively.

A collector of the NPN transistor 45c is connected to the constant voltage Vcc and an emitter thereof is connected to one terminal of the oxygen sensor S through the current detecting resistor 50a which is part of the current detecting circuit 50 and the semiconductor switch 55, and an emitter of the PNP transistor 45d is connected to the emitter of the NPN transistor 45c and a collector thereof is grounded.

A D-A converter 46 converts a bias command signal (digital signal) Vr from the microprocessor 70 to an analog signal voltage Vc. A second voltage supplying circuit 47 supplies a voltage equal to the output voltage Vc of the D-A converter 46 to the other terminal (the wire 41a to be connected to the exhaust gas side electrode layer 23) of the oxygen sensor S. The circuit 47 comprises an operational amplifier 47a in which a negative input terminal thereof is connected to the output of the D-A converter 46 and a positive input terminal thereof is connected to the other terminal of the oxygen sensor S, a resistor 47b one end of which is connected to the output terminal of the operational amplifier 47a and NPN and PNP transistors 47c and 47b whose bases are connected to the other end of the resistor 47b respectively.

Then, a collector of the NPN transistor 47c is connected to the constant voltage Vcc and an emitter thereof is connected to the other terminal of the oxygen sensor S through a resistor 47e. An emitter of the PNP transistor 47d is connected to the emitter of the NPN transistor 47c and a collector thereof is grounded.

Consequently, when the semiconductor switch 55 is in the conductive state, the constant voltage Va is always supplied to one of the terminals of the oxygen sensor S, and by supplying the bias command signal vr corresponding to a voltage lower than the constant voltage Va from the microprocessor 70 to the D-A converter 46, a voltage Vc which is lower than the constant voltage Va is supplied to the other terminal of the oxygen sensor S so that the oxygen sensor S is positively biased by the voltage of Va−Vc (Va>Vc). Furthermore, by supplying the bias command signal Vr corresponding to a voltage higher than the constant voltage Va from the microprocessor 70 to the D-A converter 46, a voltage Vc which is higher than the constant voltage Va is supplied to the other terminal of the oxygen sensor S so that the oxygen sensor S is negatively biased by the voltage of Va−Vc (Va>Vc). Thus, the bias voltage of the oxygen sensor S can be controlled to any positive or negative value based on the bias command Vr supplied from the microprocessor 70 to the D-A converter 46.

Then, a difference in voltage (Vb−Va) between both ends of the current detecting resistor 50a is inputted to the A-D converter 60 as a detected current from the current detecting circuit 50 and a difference in voltage (Va−Vc) between both ends of the oxygen sensor S is inputted to the A-D converter 60 as an induced voltage in the oxygen sensor S.

In the first embodiment thus constructed, routines for determining oxygen concentration (air-fuel ratio) and for detecting element temperature, which are executed by the microprocessor 70 when an ignition switch (not shown) is turned on will be described with reference to the flowcharts as shown in FIGS. 5–9.

FIG. 5 shows an entire control flow to be executed in the microprocessor 70 every 2 ms. Step 100 determines whether the temperature determination timing flag XTMPTM is 0. The temperature determination timing flag XTMPTM is initially set to 1 immediately after the ignition switch has been turned on. Then, if it is judged that the temperature determination timing flag XTMPTM is 0 at Step 100, an air-fuel ratio based on the threshold current in the oxygen sensor S detected by the sensor detecting circuit 50 in the air-fuel ratio (A/F) detecting routine at Step 200 is detected and then the program proceeds to Step 300. If at Step 100, it is judged that the temperature determination timing flag XTMPTM is not 0, the Step 200 is bypassed and the program proceeds to Step 300.

At Step 300, after the temperature detection timing frequency of the oxygen sensor S is determined, the program proceeds to Step 400. After the voltage applied to the oxygen sensor S is gradually changed based on the temperature detection timing frequency determined at Step 300 and the electromotive force of the oxygen sensor S is detected, the program proceeds to Step 500 and then the temperature of the oxygen sensor S is determined.

FIG. 6 shows in detail the A/F detection routine (Step 200) as shown in FIG. 5. First, the threshold current Ipos of the oxygen sensor S detected by the sensor current detecting circuit 50 at Step 201 is taken in through the A-D converter 60 and detected and then an air-fuel ration (A/F) of the internal combustion engine corresponding to the oxygen concentration is determined based on the threshold current Ipos in accordance with the characteristics stored preliminarily in the ROM at Step 202. Then the program proceeds to Step 203.

Figure 10:
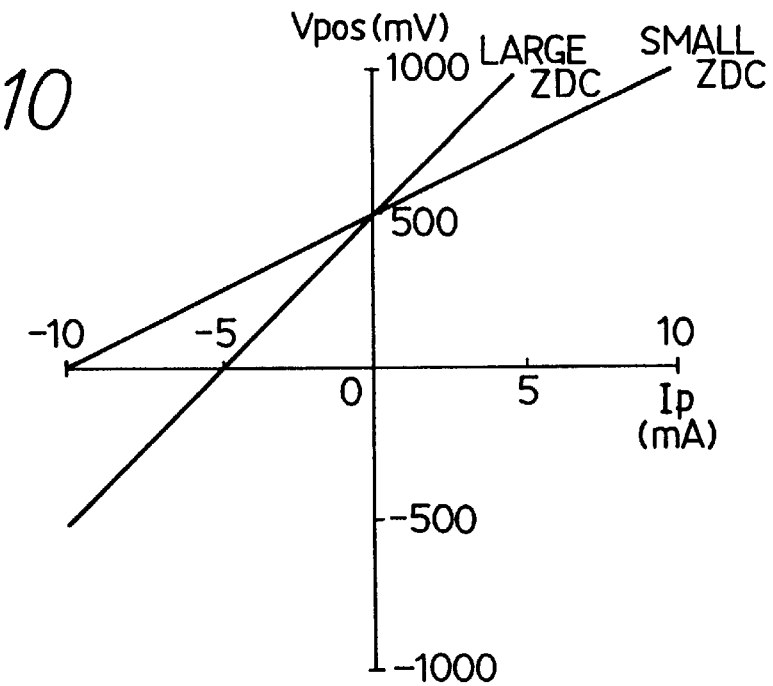
FIG. 10 is a graph of the relationship between the element DC impedance, the threshold current and a desired voltage in the first embodiment.
Figure 11:
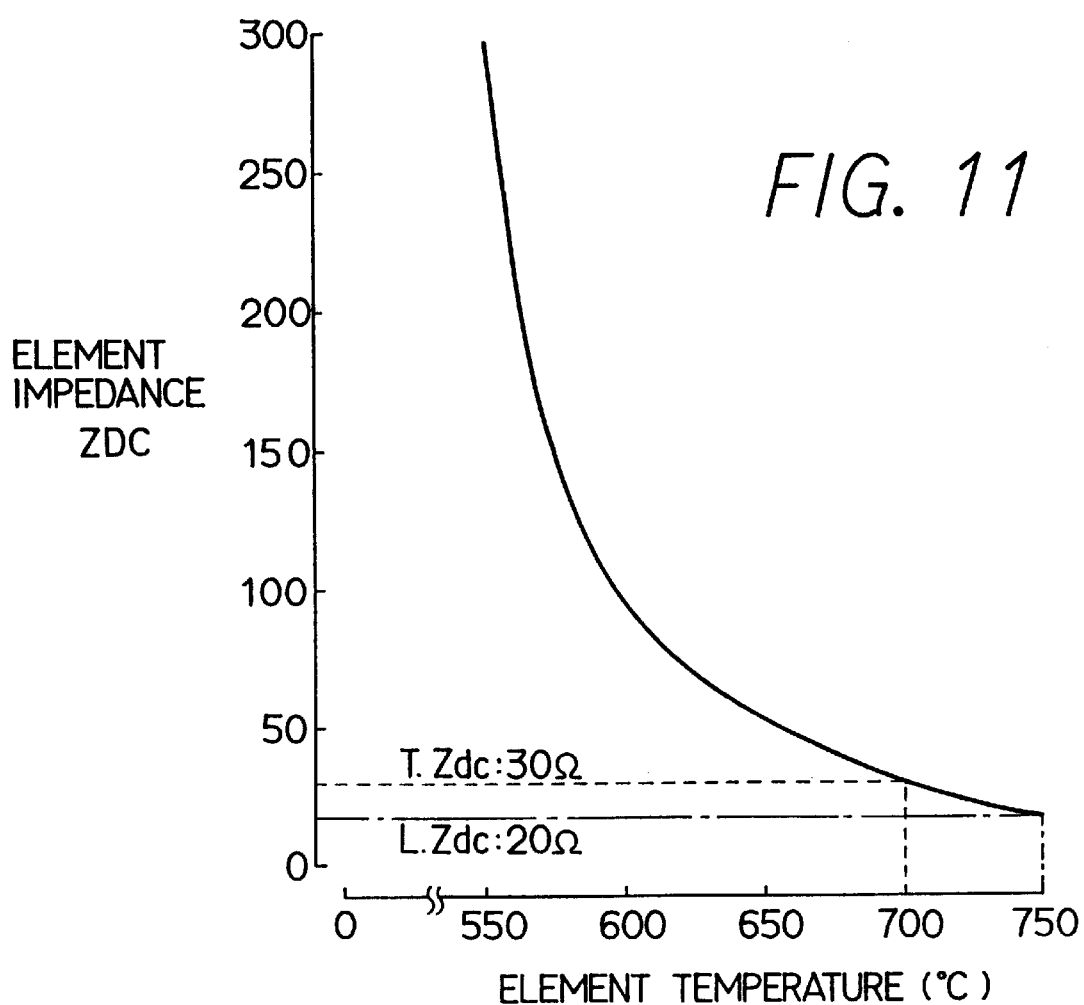
FIG. 11 is a graph of the relationship between an element temperature and the element DC impedance in the first embodiment.

At Step 203, a positive desired bias voltage (threshold current measurement voltage) Vpos is calculated from the air-fuel ratio determined at Step 202 or the threshold current Ipos detected at Step 201 and the element internal resistance ZDC (determined at Step 500), based on the characteristics preliminarily stored in the ROM as shown in FIG. 10 (the positive desired bias voltage is set in the range of, for example, 200–900 mV such that it becomes larger as the threshold current Ipos becomes larger or the air-fuel ratio becomes smaller and as the element internal resistance ZDC becomes larger or the element temperature becomes lower). Here, there is a relation between the element internal resistance (element DC impedance) ZDC and the element temperature established in which as the element temperature decreases, the element internal resistance ZDC increases drastically as shown in FIG. 11.

Figure 7:
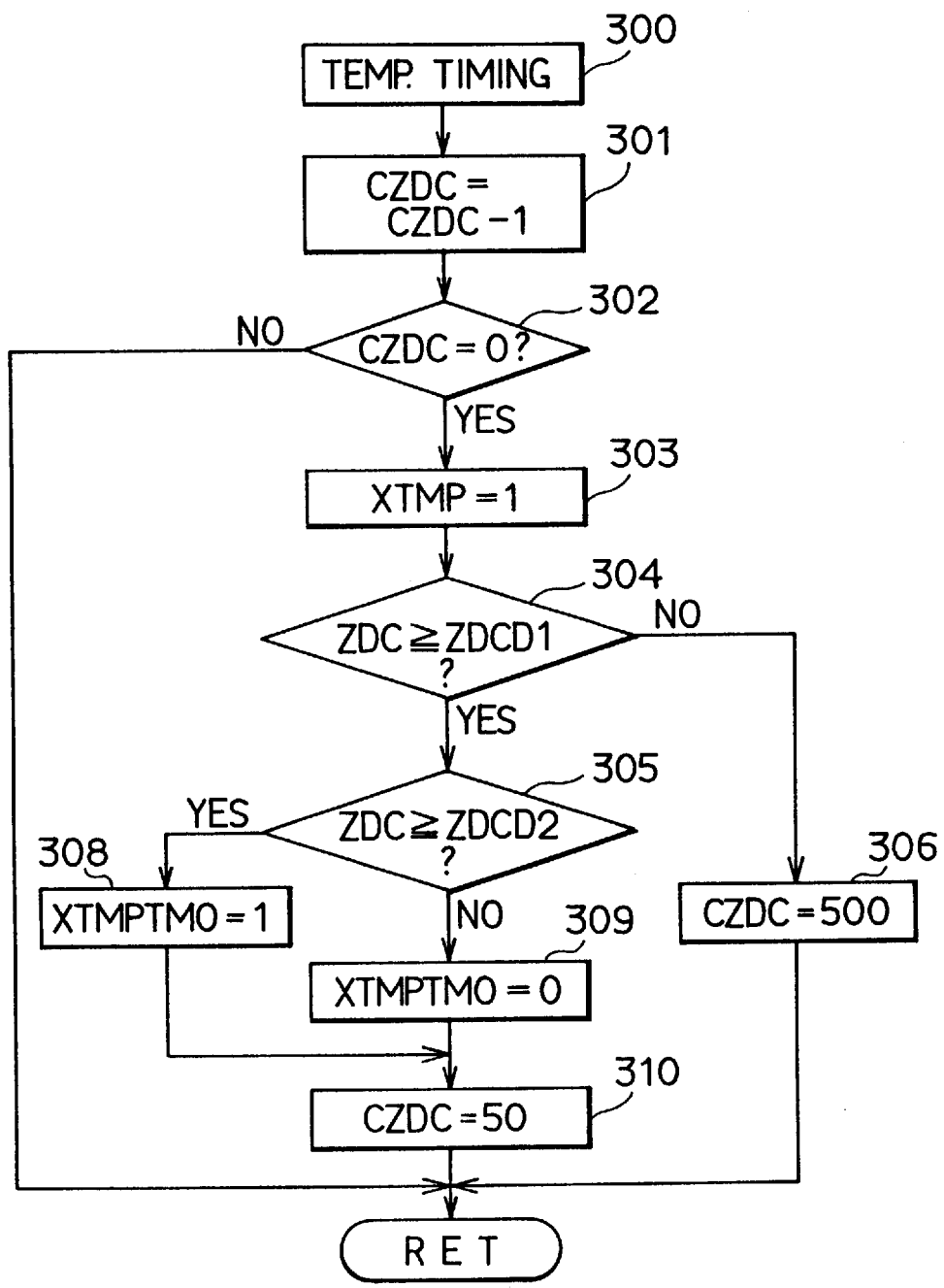

FIG. 7 shows in detail the temperature detection timing determination routine (Step 300) as shown in FIG. 5. First, at Step 301, 1 is subtracted from the temperature detection timing count value CZDC, where the temperature detection timing count value CZDC is reset to 50, that is, to 100 ms immediately after the ignition switch has been turned on. At Step 302, whether or not the temperature detection timing count value CZDC is 0 is judged. If it is judged that the temperature detection timing count value CZDC is 0 at step 302, it is time to detect the temperature. Therefore, the program proceeds to Step 303 at which a temperature detection period ON flag XTMP is set to 1, and then to Step 304. If it is judged that the temperature detection timing count value CZDC is not 0, it is not time to detect the temperature. Therefore, no operation is carried out thereafter and the temperature detection timing routine is passed through.

At Step 304, whether or not the element internal resistance ZDC is larger than a first predetermined value ZDC1 (for example, 30 Ω, which corresponds to 700° C., the temperature at which the oxygen sensor S is activated sufficiently) is judged. If at Step 304, it is judged that the element internal resistance ZDC is larger than the first predetermined value ZDC1, the program proceeds to Step 305. If at Step 304, it is judged that the element internal resistance ZDC is not larger than the first predetermined value ZDC1, it is concluded that the oxygen sensor S is not activated sufficiently. Therefore, the program proceeds to Step 306 at which the temperature detection timing count value CZDC is set to 500, that is, a relatively long period of one second. Then, the temperature detection timing routine is passed through.

Then, at Step 305, whether or not the element internal resistance ZDC is larger than a second predetermined value ZDC2 (for example, 90Ω, which corresponds to 600° C., the temperature at which the oxygen sensor S is activated to a certain extent) which is larger than a first predetermined value ZDC1 is judged. If at Step 305, it is judged that the element internal resistance ZDC is larger than the second predetermined value ZDC2, it is concluded that the oxygen sensor S is not activated. Therefore, the program proceeds to Step 308 at which the always positive bias ON flag XTMPTMO is set to 1 and then to Step 310. It is to be noted that the always positive bias ON flag XTMPTMO is initially set to 1 immediately after the ignition switch has been turned on.

If it is judged that the element internal resistance ZDC is not larger than the second predetermined value ZDC2 at Step 305, it is concluded that the oxygen sensor S is activated to a certain extent. Therefore, the program proceeds to Step 309. Then the always positive bias ON flag XTMPTMO is reset to 0 and the program proceeds to Step 310. At Step 310, the temperature detection timing count value CZDC is set to 50, that is, a relatively short period of 100 ms. Then, the temperature detection timing routine is passed through.

Figure 8:
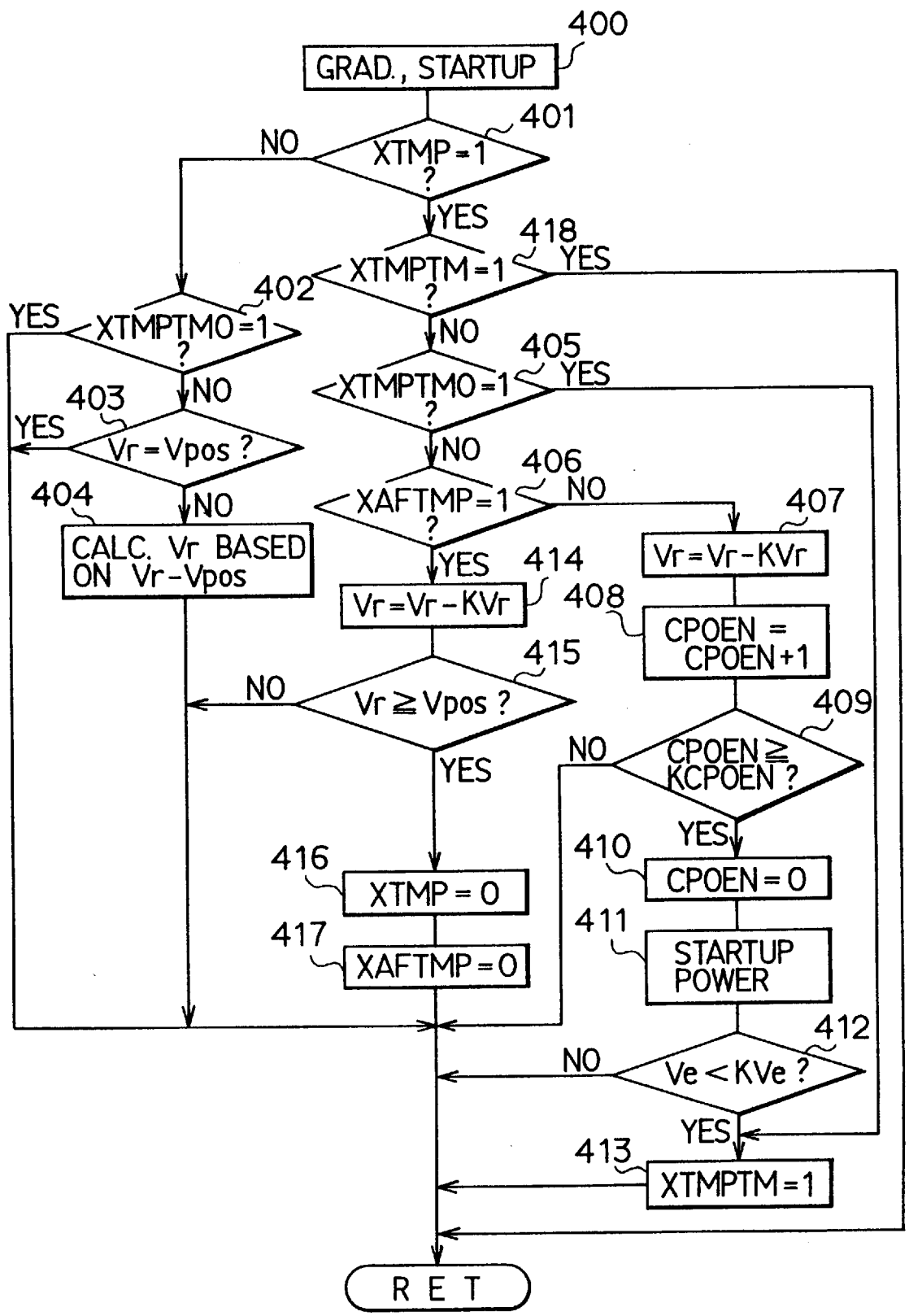

FIG. 8 shows in detail the gradual change and electromotive force determination routine (Step 400). First, at Step 401, whether or not the temperature detection period flag XTMP is 1 is judged. If it is judged that the temperature detection period flag XTMP is not 1 at Step 401, the program proceeds to Step 402, at which whether or not the always positive bias ON flag XTMPTMO is 1 is judged. If it is judged that the always positive bias ON flag XTMPTMO is not 1 at Step 402, the program proceeds to Step 403. If it is judged that the always positive bias ON flag XTMPTMO is 1 at Step 402, no operation is performed and the gradual change and electromotive force determination routine is passed through.

At Step 403, whether or not the voltage Vr supplied to the oxygen sensor S is equal to the voltage Vpos of a positive desired value is judged. If it is judged that the voltage Vr supplied to the oxygen sensor S is equal to the voltage Vpos of the positive desired value, no operation is performed and then the gradual change and electromotive force determination routine is passed through. If it is judged that the voltage Vr supplied to the oxygen sensor S is not equal to the voltage Vpos of the positive desired value, the program proceeds to Step 404 and then a voltage corresponding to a difference between the voltage Vr and the desired value Vpos is added to the voltage Vr to carry out correction so that the next-supplied voltage Vr becomes equal to the voltage Vpos of the desired value. Thereafter, the gradual change and electromotive force determination routine is passed through.

If it is judged that the temperature detection period flag XTMP is 1 at Step 401, the program proceeds to Step 418 at which whether or not the temperature determination timing flag XTMPTM is 1 is judged. If it is judged that the temperature determination timing flag XTMPTM is 1 at Step 418, it is concluded that it is time to determine the temperature. Therefore, no operation is performed and the gradual change and electromotive force determination routine is passed through. If it is judged that the temperature determination timing flag XTMPTM is not 1, it is concluded that it is not time to determine the temperature. Therefore, the program proceeds to Step 405, at which whether or not the always positive bias ON flag XTMPTMO is 1 is judged. If it is judged that the always positive bias ON flag XTMPTOMO is not 1 at Step 405, the program proceeds to Step 406, at which whether or not the after temperature determination flag XAFTMP is 1 is judged. It is to be noted that the after temperature determination flag XAFTMP is initially set to 0 immediately after the ignition switch has been turned on. If it is judged that the after temperature determination flag XAFTMP is not 1 at Step 406, the program proceeds to Step 407, at which the next-supplied oxygen sensor voltage Vr is obtained by subtracting a minute predetermined voltage Kvr (for example, 0.01 V) from the voltage Vr supplied to the oxygen sensor S. Then the program proceeds to Step 408, at which 1 is added to a voltage instantaneously interrupting count value CPOEN at Step 408, and then the program proceeds to Step 409.

At Step 409, whether or not the voltage instantaneously interrupting count value CPOEN is higher than a voltage instantaneously interrupting set value KCPOEN (for example, 4=8 ms) is judged. If it is judged that the voltage instantaneously interrupting count value CPOEN is not higher than the voltage instantaneously interrupting set value KCPOEN at Step 409, the gradual change and electromotive force determination routine is passed through. If it is judged that the voltage instantaneously interrupting count value CPOEN is higher than the voltage instantaneously interrupting set value KCPOEN at Step 409, the program proceeds to Step 410, at which the voltage instantaneously interrupting count value CPOEN is reset to 0. After that, the program proceeds to an electromotive force detection routine at Step 411.

Figure 12:
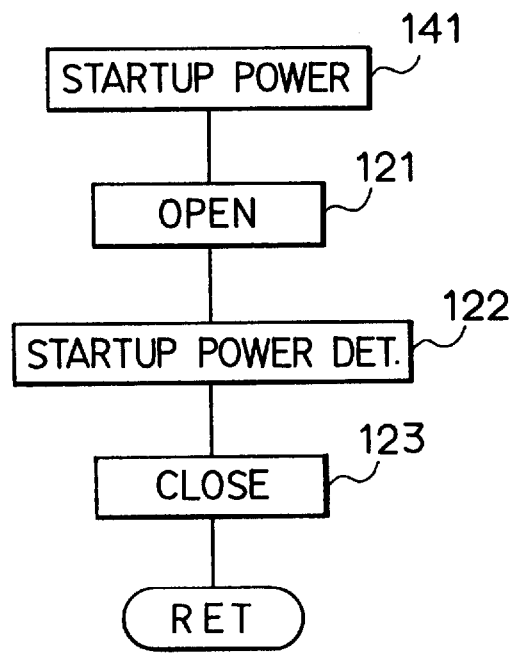
FIG. 12 is a flowchart showing the operation of the microprocessor of the first embodiment.
Figure 13:
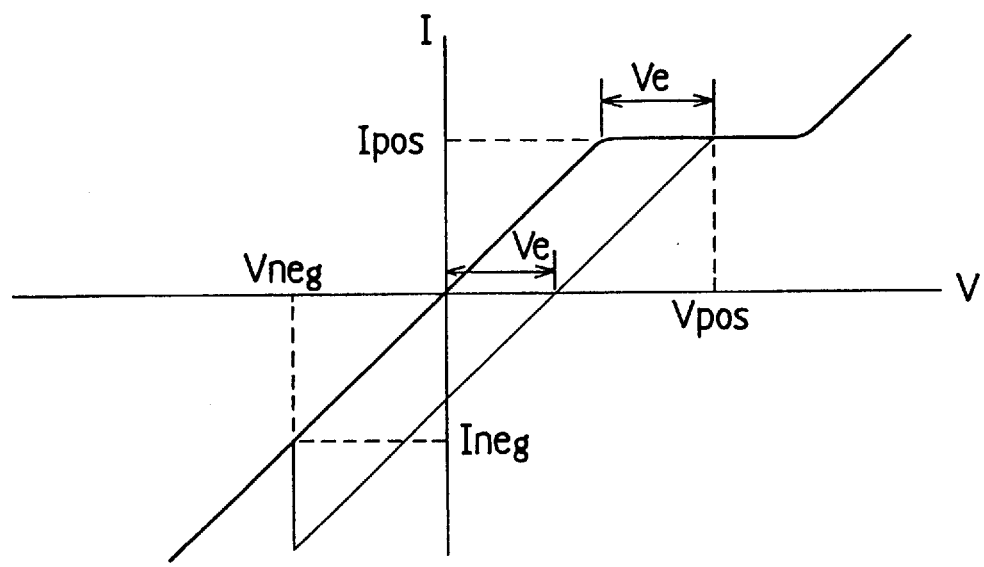
FIG. 13 is a voltage-current characteristic diagram of the oxygen sensor according to the first embodiment of the present invention.

FIG. 12 shows the electromotive force detection routine at Step 411. First, a command for blocking the semiconductor switch 55 is outputted at Step 121, and an electromotive force generated in the oxygen sensor due to blocking of the semiconductor switch 55 is detected at Step 122. Then, the program proceeds to Step 123 at which a command for bringing the semiconductor switch into a conductive state is dispatched. In this electromotive force detection routine, the semiconductor switch 55 is blocked instantaneously when the threshold current Ipos is flowing through the oxygen sensor S and then an electromotive force Ve (of the same value as the electromotive force Ve induced in the oxygen sensor S when the threshold current Ipos is flowing through the oxygen sensor S) induced in the oxygen sensor S as shown in FIG. 13 is detected.

At Step 412, whether or not the electromotive force Ve is lower than the minute set electromotive force Kve (for example, 0.02 V) is judged. If it is judged that the electromotive force Ve is lower than the minute set electromotive force Kve at Step 412, the program proceeds to Step 413 because the voltage applied to the oxygen sensor S is a value close to an end of the low voltage side within the threshold current domain and the temperature determination timing flag XTMPTM is set to 1. After that, the gradual change and electromotive force determination routine is passed through. It is to be noted that the temperature determination timing flag XTMPTM is initially set to 1 immediately after the ignition switch has been turned on. If it is judged that the electromotive force Ve is not lower than the minute set electromotive force Kve at Step 412, the gradual change and electromotive force determination routine is passed through. If it is judged that the always positive bias ON flag XTMPTMO is 1 at Step 405, the program proceeds to Step 413.

If it is judged that the after temperature determination flag XAFTMP is 1 at Step 406, the program proceeds to Step 414, at which the minute predetermined voltage Kvr (e.g., 0.01 V) is added to the voltage Vr supplied to the oxygen sensor S to obtain the next-supplied oxygen sensor voltage Vr. Then, the program proceeds to Step 415. At Step 415, whether or not the voltage Vr supplied to the oxygen sensor S is higher than the voltage Vpos of a positive desired value. If it is judged that the voltage Vr supplied to the oxygen sensor S is not higher than the voltage Vpos of the positive desired value at Step 415, the gradual change and electromotive force determination routine is passed through. If it is judged that the voltage Vr supplied to the oxygen sensor S is higher than the voltage Vpos of the positive desired value at Step 415, the program proceeds to Step 416, at which the temperature detection period flag XTMP is reset to 0. After that, the program proceeds to Step 417, at which the after temperature determination flag XAFTMP is reset to 0 and the gradual change and electromotive force determination routine is passed through.

Figure 9:
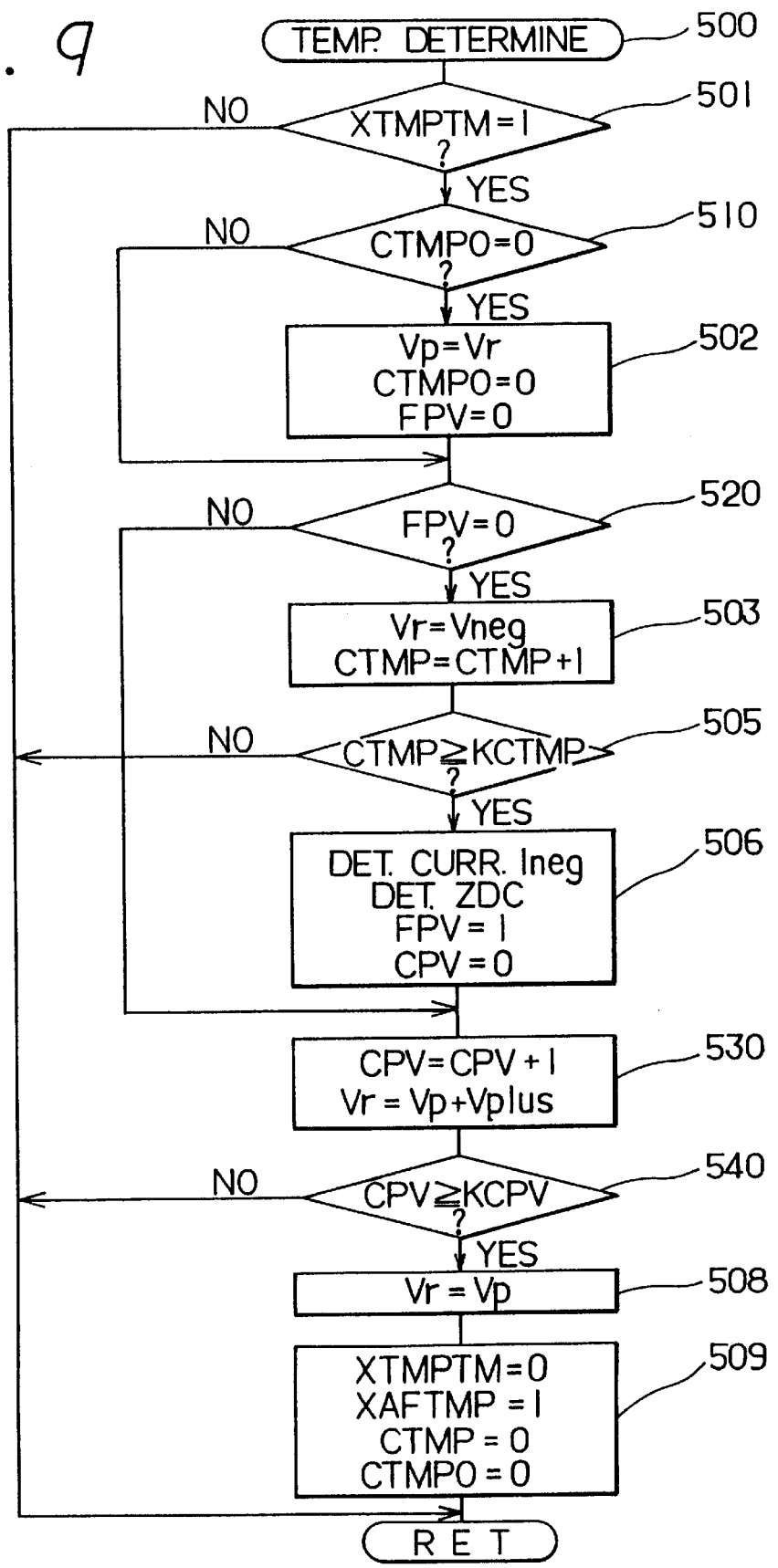

FIG. 9 shows in detail the temperature determination routine (Step 500) as shown in FIG. 5. First, at Step 501, whether or not the temperature determination timing flag XTMPTM is 1 is judged. If it is judged that the temperature determination timing flag XTMPTM is not 1 at Step 501, no operation is performed and the temperature determination routine is passed through. If it is judged that the temperature determination timing flag XTMPTM is 1 at Step 501, the program proceeds to Step 510, at which whether or not the temperature initial operation termination flag CTMPO for indicating that the initial operation following the start of the temperature detection routine has been terminated is 0 is judged.

If it is judged that the temperature initial operation termination flag CTMPO is not 0 at Step 510, the program proceeds to Step 520 because the initial operation after the temperature detection routine is entered has been terminated. If it is judged that the temperature initial operation termination flag CTMPO is 0, the program proceeds to Step 502 because the initial operation after the temperature detection routine is entered has not been terminated. At Step 502, the voltage Vr currently supplied to the oxygen sensor S is memorized as an immediately before temperature measurement voltage Vp, the temperature initial operation termination flag CTMPO is set to 1 and then the temperature detection termination flag FPV for indicating that temperature detection has been terminated is reset to 0. After that, the program proceeds to Step 520.

At Step 520, whether or not the temperature detection termination flag FPV is 0 is judged. If it is judged that the temperature detection termination flag FPV is not 0, the program proceeds to Step 530. If it is judged that the temperature detection termination flag FPV is 0, the program proceeds to Step 503. At Step 503, the voltage to be supplied to the oxygen sensor S is set to a negative temperature measurement voltage Vneg (for example, −300 mV) and 1 is added to the temperature measurement count value CTMP. After that, the program proceeds to Step 505.

At Step 505, whether or not the temperature measurement count value CTMP is higher than the temperature measurement set value KCTMP (for example, 2=4 ms) is judged. If it is judged that the temperature measurement count value CTMP is not higher than the temperature measurement set value KCTMP, the temperature determination routine is passed through. If it is judged that the temperature measurement count value CTMP is higher than the temperature measurement set value KCTMP at Step 505, the program proceeds to Step 506. At Step 506, the temperature current Ineg of the oxygen sensor S detected by the sensor current detecting circuit 50 is taken in through the A-D converter 60 and detected, and an internal resistance ZDC of the oxygen sensor S is found from an equation: ZDC=Vneg/Ineg using the temperature current Ineg and the temperature measurement voltage Vneg based on the voltage-current characteristics of the sensor as shown in FIG. 13. Then, the temperature detection termination flag FPV is set to 1 and the positive voltage application count value CPV is reset to 0.

At Step 530, 1 is added to the positive voltage application count value CPV, the voltage Vr to be supplied to the oxygen sensor S is obtained by adding a predetermined positive voltage Vplus to the immediately before temperature measurement voltage Vp memorized at Step 502, and then the program proceeds to Step 504. At Step 540, whether or not the positive voltage application count value CPV is higher than its predetermined value KCPV (e.g., 1=2 ms) is judged and if it is judged that the positive voltage application count value CPV is not higher than the predetermined value KCPV, the temperature determination routine is passed through. If it is judged that the positive voltage application count value CPV is higher than the predetermined value KCPV, the program proceeds to Step 508.

At Step 508, the voltage Vr to be supplied to the oxygen sensor S is set to the immediately before temperature measurement voltage Vp memorized at Step 502 and then the program proceeds to Step 509. At Step 509, the temperature determination timing flag XTMPTM is reset to 0, the after temperature determination flag XAFTMP is set to 1, further the temperature measurement count value CTMP is reset to 0 and the temperature initial operation termination flag CTMPO is reset to 0.

According to the above described embodiment, if the ignition switch is turned ON, because the oxygen sensor is not initially activated, a negative temperature measurement voltage Vneg is always supplied to the oxygen sensor S and the internal resistance ZDC of the oxygen sensor S is detected with a relatively low frequency of every 100 ms and the electric power of the heater 26 is controlled by means of the heater control circuit 80 based on this internal resistance ZDC, so that the oxygen sensor S is activated early.

Figure 14A:
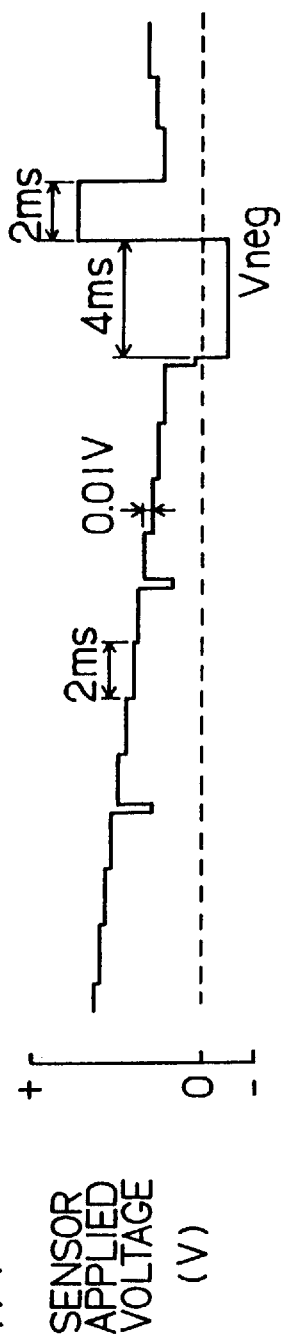
FIGS. 14A and 14B are graphs showing the action of the first embodiment.

Then, if the oxygen sensor S is activated to such an extent that the element temperature reaches 600° C., the threshold current measuring voltage Vpos of a positive desired value is supplied to the oxygen sensor S, so that the threshold current Ipos of the oxygen sensor S or the air-fuel ratio of the internal combustion engine (concentration of oxygen in exhaust gas) is detected with the frequency of every 2 ms. In this period, with a relatively low temperature detection frequency of every 100 ms, as shown in FIG. 14A, the supply voltage of the oxygen sensor S gradually decreases from the voltage Vpos of a positive desired value by 0.01 V every 2 ms and then the supply voltage of the oxygen sensor S is instantaneously interrupted every 8 ms, so that the electromotive force Ve induced in the oxygen sensor S is detected in this interruption period.

Figure 14B:
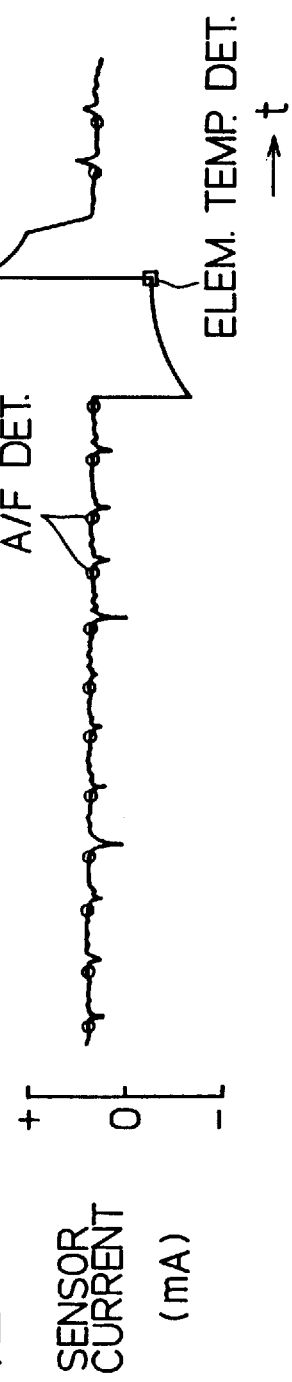

If the electromotive force is lower than the minute set voltage of 0.02 V, a negative temperature measuring voltage Vneg is supplied to the oxygen sensor S and 4 ms after that, the internal resistance ZD of the oxygen sensor S or the element temperature is detected. After that, a voltage obtained by adding the positive voltage Vplus to the immediately before temperature measurement voltage Vp, supplied to the oxygen sensor S just before the temperature measurement voltage Vneg is supplied, is supplied to the oxygen sensor S for a short period of 2 ms. After that, the voltage supplied to the oxygen sensor S is increased gradually by 0.01 V every 2 ms from the voltage immediately before the temperature measurement Vp until it reaches a positive desired threshold current measurement voltage Vpos. With the control of a voltage supplied to the oxygen sensor S as described above, the current as described in FIG. 14B flows to the oxygen sensor S. After that as well, with a frequency of every 2 ms, the threshold current Ipos of the oxygen sensor S or the air-fuel ratio of the internal combustion engine is almost continuously detected. Furthermore, with a relatively short frequency of every 100 ms, the element internal resistance ZDC or the element temperature is detected. Here, a period during which the air-fuel ratio cannot be detected with the frequency of every 2 ms is only 8 ms during detection of the element temperature.

Furthermore, because the change of the element temperature decreases if the oxygen sensor S is sufficiently activated so that the element temperature reaches 700° C., the temperature detection cycle is changed from every 100 ms to a relatively long period of every 1 second. In the same manner as described above, the air-fuel ratio is almost continuously detected with the frequency of every 2 ms. By prolonging the temperature detection frequency like this, it is possible to increase the opportunity of detecting the air-fuel ratio.

Figure 15:
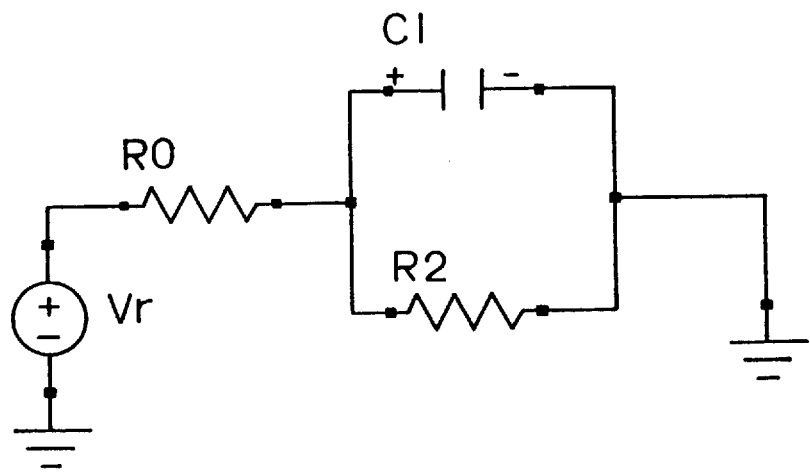
FIG. 15 is an equivalent electric circuit diagram of the oxygen sensor according to the first embodiment.

The electric equivalent circuit of the oxygen sensor S can be represented as shown in FIG. 15. Referring to FIG. 15, R0 corresponds to an internal resistance in a resistance controlling domain (domain in which a current flows between both electrodes of the oxygen sensor S proportional to the voltage Vr to be applied in between the electrode terminals of the oxygen sensors S) and R2 indicates a resistance existing in an interface between an electrolyte and an electrode in the overvoltage domain (domain in which a substantially constant threshold current flows between both electrodes of the oxygen sensor S irrespective of the voltage Vr to be applied between the electrode terminals of the oxygen sensor S). C1 indicates the electrostatic capacitance of the interface. Thus, when the overvoltage domain is changed to the resistance controlling domain to measure the internal resistance when measuring the threshold current or when the resistance controlling domain is changed to the overvoltage domain to measure the threshold current after measuring the internal resistance, as shown in FIG. 16, the sensor current converges to a stable value a predetermined time after a peak in positive and negative values respectively appears, because of influence of electric charge accumulated in the electrostatic capacitance C1 in the interface.

Here, each peak value at the time of a change of the voltage can be decreased, as described in the flow shown in FIG. 8, by increasing or decreasing gradually the voltage applied to the oxygen sensor S so as to reduce the electromotive force induced in the oxygen sensor S at the time of the change of the voltage. Consequently, the stabilization time of the sensor current can be reduced. In addition, as described about the flow of FIG. 9, by supplying the voltage obtained by adding a predetermined positive voltage Vplus to the immediately before temperature measurement voltage Vp, to the oxygen sensor S in a short time when the resistance controlling domain is changed to the overvoltage domain, discharge and recharge of electric charge in the electrostatic capacitance C1 in the interface is terminated quickly, so that the stabilization time of the sensor current can be reduced more.

Then, as the predetermined positive voltage Vplus, any constant value of 0.2 to 0.8 V is applicable or the value may vary depending on a detected threshold current value. The period during which the voltage obtained by adding the predetermined positive voltage Vplus to the voltage immediately before the temperature measurement Vp is applied to the oxygen sensor S for a short time may be about 1 to 2 ms. However, there is a relationship established in which as one of the period and the predetermined positive voltage Vplus is increased, the other can be decreased. By balancing both of them, it is possible to effectively reduce the period during which the detection is impossible.

Figure 1A:
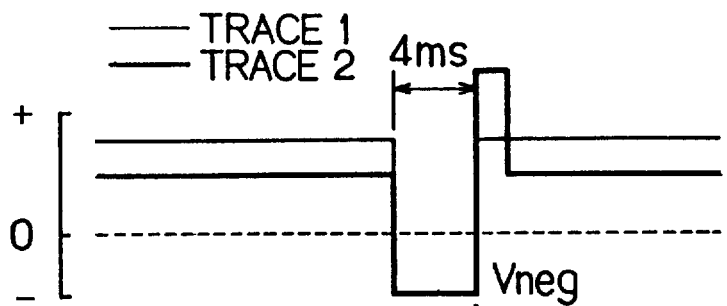
FIG. 1A is a waveform diagram showing a sensor application voltage.
Figure 1B:
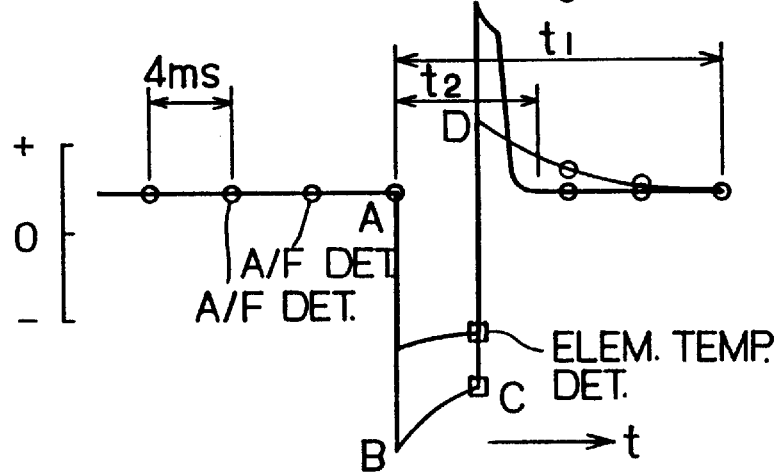
FIG. 1B is a waveform diagram showing a sensor current and FIG. 1C is a voltage-current characteristic diagram of an oxygen sensor.
Figure 1C:
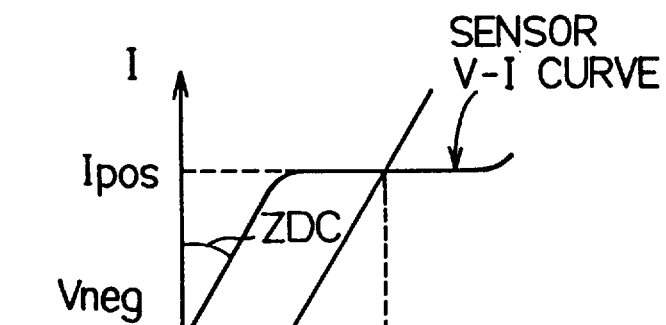
Figure 16:
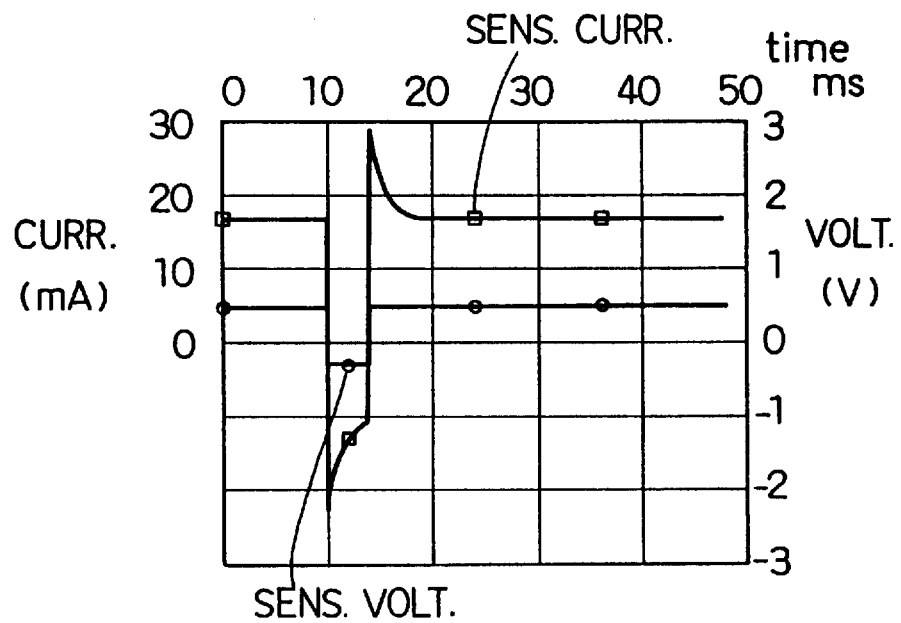
FIG. 16 is a sensor current/voltage waveform diagram of a comparative example.
Figure 17:
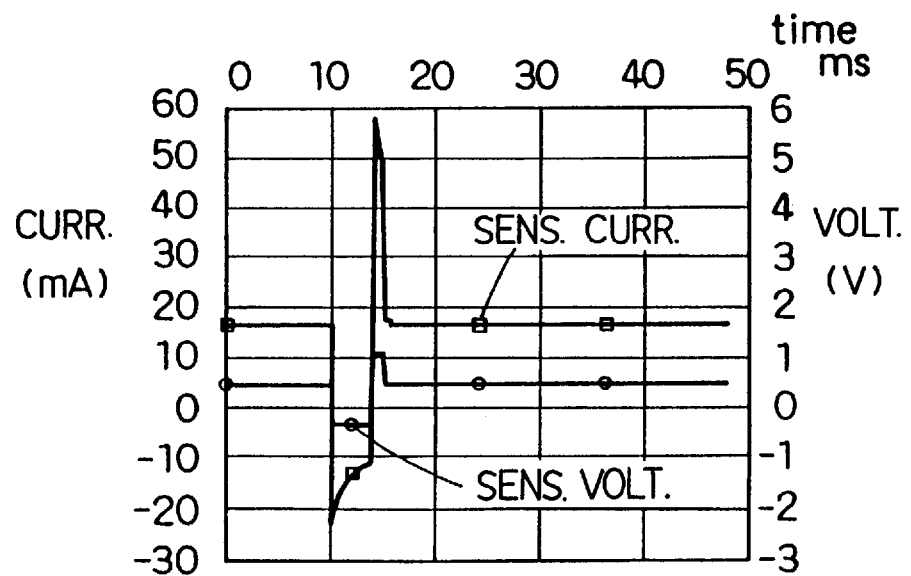
FIG. 17 is a sensor current/voltage waveform diagram of the first embodiment.

Here, FIG. 16 shows the sensor current and voltage characteristics of a comparison case in which Steps 530, 540 are omitted from the flow of FIG. 9. While it takes longer than 5 ms until the sensor current converges to its stable state when the resistance controlling domain is changed to the overvoltage domain, in this embodiment, the sensor current is stabilized to its converged value substantially at the same time when addition of the predetermined positive voltage Vplus is terminated as shown in FIG. 17 and by a locus 2 in FIG. 1, so that the time taken until the sensor current is stabilized to its converging value can be reduced to lower than half as compared to the comparison example.

According to the above-described embodiment, although a negative constant voltage is supplied to the oxygen sensor S as a temperature measurement voltage at Step 503 in FIG. 9, a voltage obtained by subtracting a predetermined voltage from a voltage immediately before supply of the temperature measurement voltage may be supplied as a temperature measurement voltage.

Furthermore, according to the above-described embodiment, although the temperature measurement voltage is set to a voltage lower than the threshold current measuring voltage, conversely the temperature measurement voltage may be higher than the threshold current measuring voltage. In this case, when the temperature measurement voltage is changed to the threshold current measuring voltage, a predetermined positive voltage may be added for a short time instead of the predetermined positive voltage when the temperature measurement voltage is changed to the threshold current measuring voltage.

Furthermore, according to the above-described embodiment, although the voltage applied to the oxygen sensor S is gradually decreased or increased in the gradual change and electromotive force routine as shown in FIG. 8 and induced in the oxygen sensor S at the time of a change in the voltage so as to decrease the electromotive force to a predetermined value, decrease the peak voltage, and reduce the period during which the detection is impossible, the gradual change and electromotive force routine as shown in FIG. 8 may be omitted and the present invention may be applied to an estimation of convergence current by detecting a current being converged as described in U.S. Pat. No. 5,405,521.

Furthermore, according to the above described embodiment, although at Step 506 in FIG. 9, the internal resistance ZDC of the oxygen sensor S is detected by arithmetic operation of ZDC=Vneg/Ineg, based on the sensor voltage-current characteristics, using the temperature current Ineg and the temperature measuring voltage Vneg which appear when the temperature measuring voltage is supplied to the oxygen sensor S, it is permissible to detect the internal resistance ZDC of the oxygen sensor S based on ZDC=(Vpos−Vneg)/(Ipos−Ineg), using the threshold current measuring voltage Vpos immediately before the temperature measuring voltage is applied and the threshold current Ipos immediately before the temperature measuring voltage is applied. Thus, it is possible to omit the gradual change and electromotive force routine shown in FIG. 8.

The bias control circuit 40, Step 203 correspond to the threshold current measuring voltage supply means of the present invention. The bias control circuit, Step 503 correspond to the temperature measuring voltage supply means thereof. Steps 508, 530, 540 correspond to the voltage change-over control means thereof and Step 201 corresponds to the threshold current detecting means. Step 506 corresponds to the element temperature detecting means and the internal resistance detecting means. Steps 407–412 correspond to the voltage damping means and Steps 301, 303–310 correspond to the frequency determining means thereof.

Second embodiment

Next, the second embodiment of the oxygen sensor (A/F sensor) will be explained. However, the description will be focused on what is different from the A/F sensor according to the first embodiment.

Although in the first embodiment of the A/F sensor, the air-fuel ratio detecting device is constructed using the cup-shaped A/F sensor S to detect A/F from threshold current flowing as the voltage is applied to the sensor 30, according to this embodiment of the A/F sensor, the air-fuel ratio detecting device is constructed using an integrated type A/F sensor SA instead of the A/F sensor S. Hereinafter, the construction and the characteristics of the integrated type A/F sensor will be explained with reference to drawings.

Figure 18:
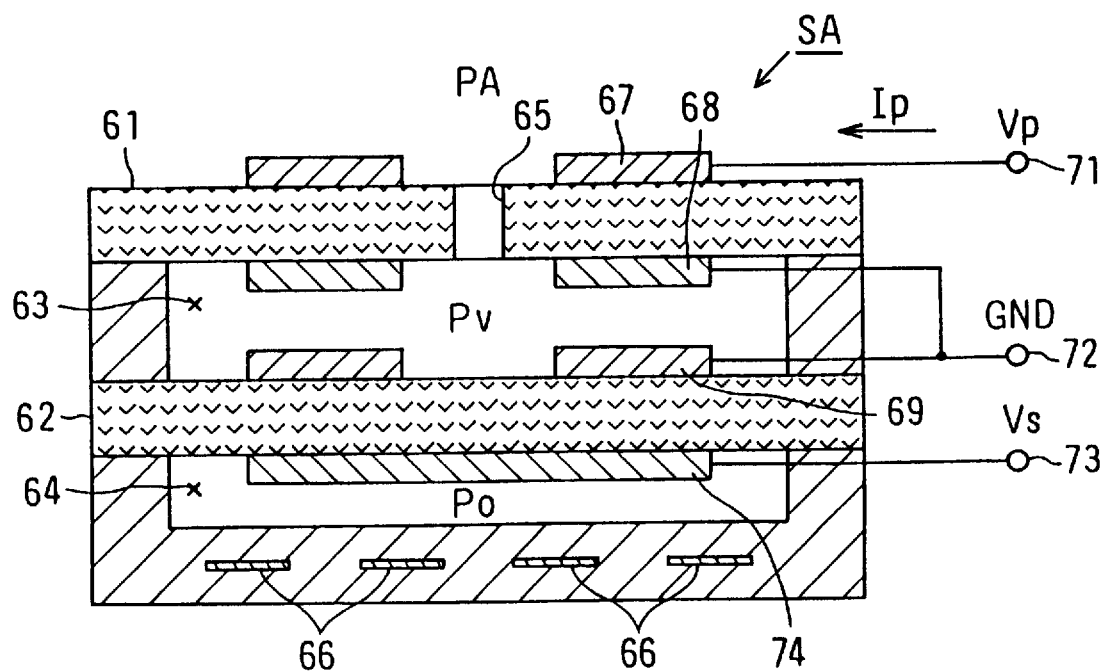
FIG. 18 is a cross-sectional view of an integrated type A/F sensor according to a second embodiment of the present invention.

FIG. 18 shows the cross-section of the integrated type A/F sensor SA. The integrated type A/F sensor SA includes two solid electrolyte layers 61, 62 made of zirconia, which are generally respectively referred to as a pumping cell (solid electrolyte layer 61) and a sensing cell (solid electrolyte layer 62). A diffusion gap 63 is disposed as an oxygen concentration determination chamber below the solid electrolyte layer 61 and an air duct 64 is disposed as an atmospheric pressure chamber below the solid electrolyte layer 62. A pin hole 65 is formed in the solid electrolyte layer 61 such that exhaust gas is introduced into the diffusion gap 63 through this pin hole 65. The reference numerals 66 indicate heaters for heating the sensor SA.

Platinum electrodes 67, 68 are mounted on the upper and lower surfaces of the solid electrolyte layer 61 (pumping cell) and platinum electrodes 69, 74 are mounted on the upper and lower surfaces of the solid electrolyte layer 62 (sensing cell). A terminal 71 is connected to an electrode 67, a terminal 72 is connected to electrodes 68, 69 and a terminal 73 is connected to an electrode 74.

Figure 19:
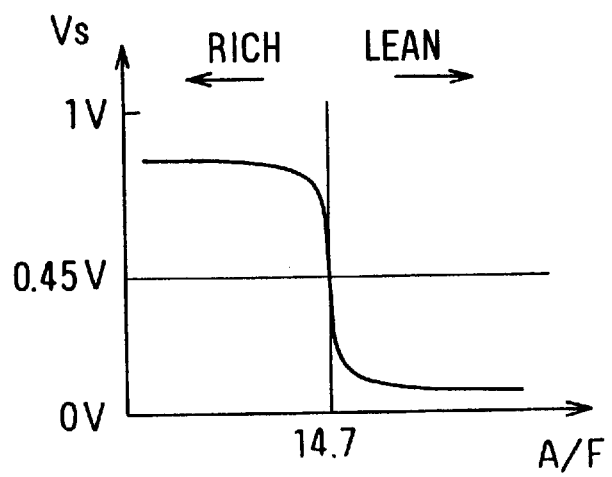
FIG. 19 is a graph showing the relationship between the A/F and electromotive force of the integrated type A/F sensor according to the second embodiment.

The operating principle of this integrated type A/F sensor SA will be described below. FIG. 19 is a graph showing the characteristics of the sensor electromotive force Vs generated between the terminals 72 and 73. At this time, the sensor electromotive force Vs is determined by the oxygen concentration Pv within the diffusion gap 63 and the oxygen concentration (equal to the oxygen concentration in the atmosphere) within the air duct 64, as shown in Equation (1) below.

$$V_S = \frac{RT}{4F} \cdot \ln\left(\frac{P_o}{P_v}\right) \quad (1)$$

Here, R is the gas constant, T is absolute temperature and F is Faraday constant.

Furthermore, the oxygen concentration Pv in the diffusion gas 63 is usually equal to the oxygen concentration PA of exhaust gas. Thus, if the A/F becomes rich so that the oxygen concentration PA in exhaust gas decreases, the oxygen concentration Pv in the diffusion gap 63 also decreases, so that the sensor electromotive force Vs increases. Conversely, if the A/F becomes lean, the oxygen concentration Pv in the diffusion gap 63 increases, so that the sensor electromotive force Vs decreases. Then, this sensor electromotive force Vs is detected by the terminal 73.

Furthermore, by applying the voltage Vp to the terminal 71 to make the pumping current Ip flow, oxygen ions pass through the solid electrolyte layer 61, so that the oxygen concentration Pv in the diffusion gap 63 can be controlled freely. According to the above described principle, by detecting the sensor electromotive force Vs and then controlling the voltage Vp to be applied to the terminal 71 so that value becomes constant, it is possible to detect the oxygen concentration of exhaust gas or the A/F ratio from the pumping current Ip.

Figure 20:
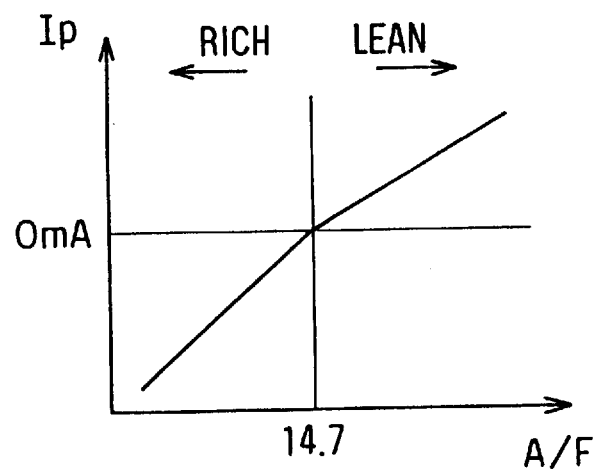
FIG. 20 is a graph showing the relationship between the A/F and the pumping current of the integrated type A/F sensor according to the second embodiment.

That is, the oxygen concentration Pv in the diffusion gap 63 must be made to be always constant oxygen concentration Pvo in order to control the sensor electromotive force Vs at a constant level. For this purpose, the amount of oxygen corresponding to a difference between the oxygen concentration PA in exhaust gas and Pvo needs to be supplied. At this time, the amount of oxygen corresponding to the difference between PA and Pvo is determined by the magnitude of the pumping current Ip. Thus, the oxygen concentration (A/F) of exhaust gas can be detected from the pumping current Ip. If as shown in FIG. 19, the sensor electromotive force Vs when A/F=14.7 (however, it varies slightly depending on engine type) is controlled to be its predetermined value (Vs=0.45 V), the characteristics of the pumping current Ip and the A/F are such that A/F=14.7 and Ip =0 mA as shown in FIG. 20. The characteristic diagram shown in FIG. 20 indicates that the positive side pumping current Ip flows if the A/F becomes lean and the negative side pumping current Ip flows if the A/F becomes rich.

Figure 21:
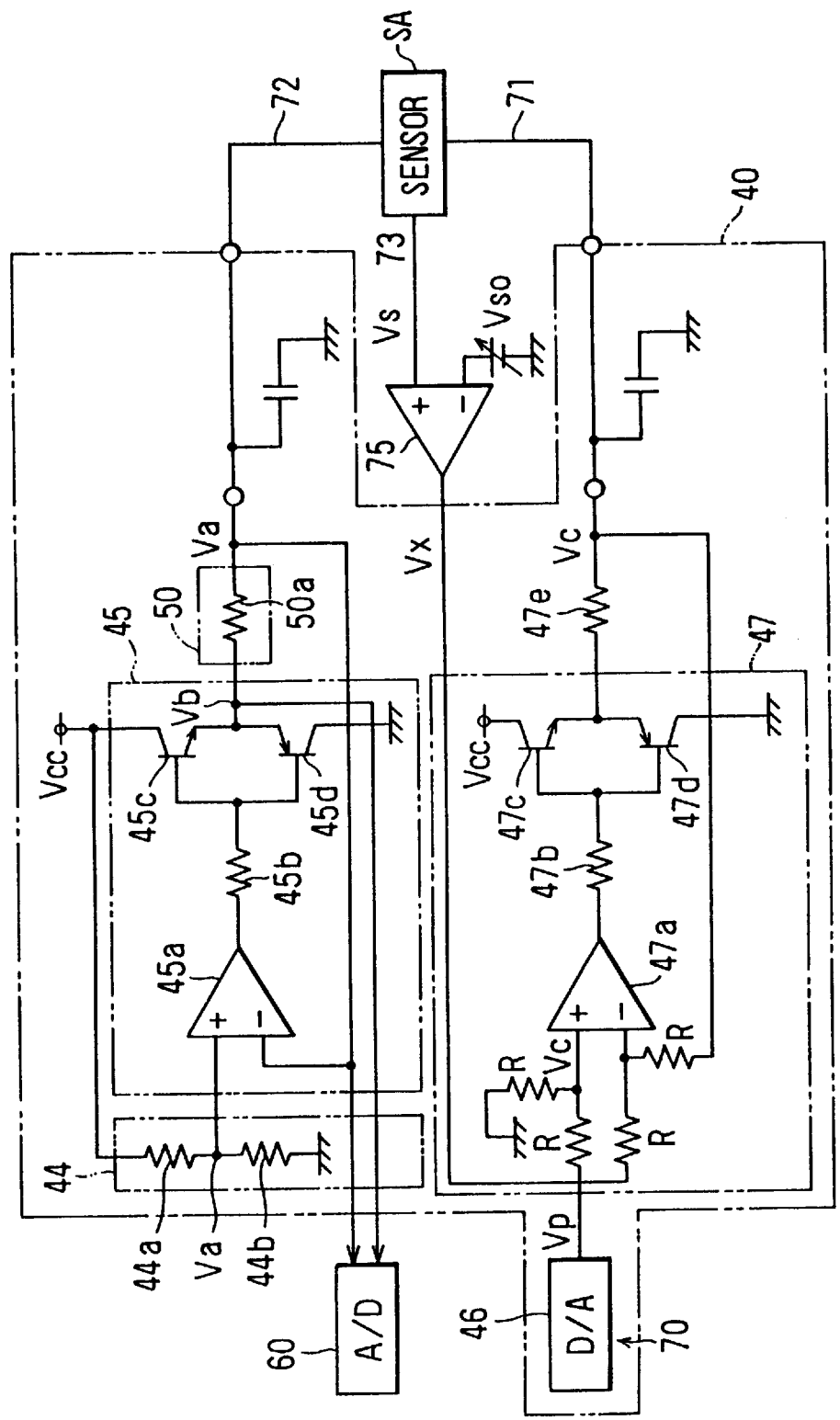
FIG. 21 is a schematic diagram showing the construction of the bias control circuit in the integrated type A/F sensor according to the second embodiment.

FIG. 21 shows an electric circuit including the bias control circuit 40 according to this embodiment of the present invention. Hereinafter, only different points from an embodiment in which the cup-shaped sensor is used will be described below.

In addition to the terminals 71, 72 (equivalent to the terminals 41a, 42b in the above FIG. 4) for element application voltage, the integrated type A/F sensor SA includes another terminal 73 for electromotive force detection. In this case, the sensor electromotive force Vs is detected from the terminal 73, the operational amplifier 75 compares the sensor electromotive force Vs with the reference voltage Vso and its comparison result is amplified and output. Furthermore, the amplified signal is supplied to the second voltage supply circuit 47 and a difference from a signal from the D-A converter 46 is obtained. That is, as compared with the first embodiment in which the cup-shaped sensor is used, the second voltage supply circuit 47 has been changed from a voltage follower circuit to a differential amplifier circuit. Furthermore, as compared with FIG. 4, the semiconductor switch 55 is omitted and thus use of the variation and electromotive force routine shown in FIG. 8 is canceled to detect the A/F and element resistance.

In this circuit, the reference voltage Vso for comparison in the operational amplifier 75 is adjusted as follows. That is, in the present embodiment, it is adjusted so that Ip=0 mA when A/F=14.7. In other words, when A/F=14.7, the voltage at the terminal 71 must be the same as that of the terminal 72 and if the voltage for detecting an output from the D-A converter 46 is assumed to be Vp, the reference voltage Vso for comparison is adjusted so that the output Vx of the operational amplifier 75 is (Vp−Va).

According to the construction of this circuit, if an exhaust gas becomes rich, the sensor electromotive force Vs at the terminal 73 increases so that the output of the operational amplifier 75 increases. Then, the output Vc of the second voltage supply circuit 47 decreases so that the voltage applied to the terminal 71 decreases. Consequently, the pumping current Ip flows in a direction opposite to that as shown in FIG. 18 (the minus pumping current Ip flows), so that oxygen is supplied to the diffusion gap 63. On the other hand, if the exhaust gas becomes lean, the plus pumping current Ip flows and at the same time, oxygen in the diffusion gap 63 is pumped out.

Then, in the air-fuel ratio detecting device having the above-described construction according to the present embodiment, the element temperature of the integrated type A/F sensor SA can be detected in the same procedure as in the first embodiment. Furthermore, when switching from the temperature measuring voltage to the current measuring voltage after the element temperature is detected, by supplying a voltage in a direction opposite to the temperature measuring voltage for a short time and then restoring it to the current measuring voltage, it is possible to effectively reduce the time during which the oxygen concentration cannot be detected.

Although the present invention has been fully described in connection with the preferred embodiment thereof with reference to the accompanying drawings, it is to be noted that various changes and modifications will become apparent to those skilled in the art. Such changes and modifications are to be understood as being included within the scope of the present invention as defined by the appended claims.

What is claimed is:

1. An oxygen concentration measuring device comprising:
    an oxygen sensor;
    threshold current measuring voltage supplying means for generating a threshold current measuring voltage;
    temperature measuring voltage supplying means for generating a temperature measuring voltage different from said threshold current measuring voltage;
    voltage change-over control means for (a) receiving said threshold current measuring voltage and said temperature measuring voltage, (b) providing said threshold current measuring voltage to said oxygen sensor as successive different voltages so as to more rapidly cause convergence to a stable current value for measurement and (c) subsequently providing said temperature measuring voltage to said oxygen sensor as a voltage which is one of a higher voltage and a lower voltage than said threshold current measuring voltage for a short period of time prior to temperature measurement;
    threshold current detecting means for detecting a threshold current flowing through said oxygen sensor when said voltage change-over control means provides said threshold current measuring voltage to said oxygen sensor; and
    temperature detecting means for detecting a temperature of said oxygen sensor based on a current flowing through said oxygen sensor when said voltage change-over control means provides said temperature measuring voltage to said oxygen sensor.

2. The oxygen concentration measuring device of claim 1, further comprising:
    voltage reducing means for reducing gradually said threshold current measuring voltage from a desired value until an electromotive force generated in said oxygen sensor in a vicinity of an occurrence limit of said threshold current becomes lower than a predetermined value when said threshold current is detected;
    wherein said temperature measuring voltage supplying means is further for supplying said temperature measuring voltage to said oxygen sensor if the voltage supplied to said oxygen sensor decreases to the predetermined value in the vicinity of the occurrence limit of said threshold current.

3. The oxygen concentration measuring device of claim 2, said temperature detecting means comprising internal resistance detecting means for determining an internal resistance ZDC of the oxygen sensor based on an equation ZDC= Vneg/Ineg in which Vneg denotes a temperature measuring voltage and Ineg denotes a temperature current generated when the temperature measuring voltage Vneg is supplied to the oxygen sensor.

4. The oxygen concentration measuring device of claim 3, further comprising frequency determining means for repeatedly controlling said temperature detecting means to detect the threshold current at a frequency lower than a frequency of temperature detection by said temperature detecting means.

5. The oxygen concentration measuring device of claim 2, further comprising frequency determining means for repeatedly controlling said temperature detecting means to detect the threshold current at a frequency lower than a frequency of temperature detection by said temperature detecting means.

6. The oxygen concentration measuring device of claim 1, said temperature detecting means comprising internal resistance detecting means for determining an internal resistance ZDC of the oxygen sensor based on an equation ZDC= Vneg/Ineg in which Vneg denotes a temperature measuring voltage and Ineg denotes a temperature current generated when the temperature measuring voltage Vneg is supplied to the oxygen sensor.

7. The oxygen concentration measuring device of claim 6, further comprising frequency determining means for repeatedly controlling said temperature detecting means to detect the threshold current at a frequency lower than a frequency of temperature detection by said temperature detecting means.

8. The oxygen concentration measuring device of claim 1, said temperature detecting means comprising internal resistance detecting means for determining an internal resistance ZDC of the oxygen sensor based on an equation: ZDC= (Vpos−Vneg)/(Ipos−Ineg) in which Vneg and Ineg respectively denote a temperature measuring voltage and a temperature current when the temperature measuring voltage is supplied to the oxygen sensor, Vpos denotes a threshold current measuring voltage immediately before the temperature measuring voltage is applied, and Ipos denotes a threshold current immediately before the temperature measuring voltage is applied.

9. The oxygen concentration measuring device of claim 8, further comprising frequency determining means for repeatedly controlling said temperature detecting means to detect the threshold current at a frequency lower than a frequency of temperature detection by said temperature detecting means.

10. The oxygen concentration measuring device of claim 1, further comprising frequency determining means for repeatedly controlling said temperature detecting means to detect the threshold current at a frequency lower than a frequency of temperature detection by said temperature detecting means.

11. An oxygen concentration measuring device comprising:
    oxygen sensing means for generating a current corresponding to oxygen concentration of a detected gas in response to application of a voltage thereto;
    threshold current measuring voltage supplying means for generating a threshold current measuring voltage;
    temperature measuring voltage supplying means for generating a temperature measuring voltage different from said threshold current measuring voltage;
    voltage change-over control means for (a) receiving said threshold current measuring voltage and said temperature measuring voltage and (b) subsequently providing said temperature measuring voltage to said oxygen sensing means as one of a higher voltage and a lower voltage than said threshold current measuring voltage for a short period of time prior to temperature measurement;

threshold current detecting means for detecting a threshold current flowing through said oxygen sensing means when said voltage change-over control means provides said threshold current measuring voltage to said oxygen sensing means; and temperature detecting means for detecting a temperature of said oxygen sensing means based on a current flowing through said oxygen sensing means when said voltage change-over control means provides said temperature measuring voltage to said oxygen sensing means.

12. An oxygen concentration measuring device comprising:

an oxygen sensor having an equivalent circuit with an internal resistance parameter related to temperature and internal RC parameters related to constant current oxygen concentration measurement;

a cyclic bi-polar voltage supply connected to said oxygen sensor for periodically biasing the sensor with a first polarity voltage to measure temperature and then with a second polarity voltage to measure oxygen concentration as a quiescent constant current;

said cyclic bi-polar voltage supply including means for temporarily over-biasing the sensor with a higher second polarity voltage to more rapidly change the stored charge in said RC parameters and thus more quickly revert to an oxygen concentration measuring mode.

13. An oxygen concentration measuring device as in claim 12 wherein:

said cyclic bi-polar voltage supply further includes means for gradually reducing the bias voltage of said second polarity until an electromotive force generated in the sensor reaches a predetermined value before switching to said first polarity to measure temperature thereby also reducing the time required to effect a temperature measurement.

14. An oxygen concentration measuring method comprising:

exposing to an engine exhaust stream an oxygen sensor having an equivalent circuit with an internal resistance parameter related to temperature and internal RC parameters related to constant current oxygen concentration measurement;

periodically biasing the sensor with a first polarity voltage to measure temperature and then with a second polarity voltage to measure oxygen concentration as a quiescent constant current;

temporarily over-biasing the sensor with a higher second polarity voltage to more rapidly change the stored charge in said RC parameters and thus more quickly revert to an oxygen concentration measuring mode.

15. An oxygen concentration measuring method as in claim 14 wherein:

gradually reducing the bias voltage of said second polarity until an electromotive force generating in the sensor reaches a predetermined value before switching to said first polarity to measure temperature thereby also reducing the time required to effect a temperature measure.

* * * * *